United States Patent
Lee et al.

(10) Patent No.: US 11,542,483 B2
(45) Date of Patent: Jan. 3, 2023

(54) RECOMBINANT MICROORGANISM CAPABLE OF GROWING USING ONLY CARBON DIOXIDE AND FORMIC ACID AND METHOD FOR PRODUCING USEFUL SUBSTANCES USING THE RECOMBINANT MICROORGANISM

(71) Applicant: KOREA ADVANCED INSTITUTE OF SCIENCE AND TECHNOLOGY, Daejeon (KR)

(72) Inventors: Sang Yup Lee, Daejeon (KR); Junho Bang, Daejeon (KR); Chang Hun Hwang, Daejeon (KR); Jung Ho Ahn, Daejeon (KR); Jong An Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 17/366,269

(22) Filed: Jul. 2, 2021

(65) Prior Publication Data
US 2022/0017879 A1 Jan. 20, 2022

(30) Foreign Application Priority Data
Jul. 14, 2020 (KR) .................. 10-2020-0086811

(51) Int. Cl.
| | |
|---|---|
| C12P 7/46 | (2006.01) |
| C12N 9/10 | (2006.01) |
| C12P 7/02 | (2006.01) |
| C12N 9/04 | (2006.01) |
| C12N 9/00 | (2006.01) |
| C12N 9/78 | (2006.01) |
| C12P 7/16 | (2006.01) |
| C12P 7/04 | (2006.01) |
| C12P 13/10 | (2006.01) |
| C12P 5/00 | (2006.01) |
| C12P 5/02 | (2006.01) |
| C12P 13/00 | (2006.01) |
| C12P 7/42 | (2006.01) |
| C12P 17/10 | (2006.01) |
| C12P 13/06 | (2006.01) |
| C12P 13/08 | (2006.01) |

(52) U.S. Cl.
CPC ......... *C12N 9/1029* (2013.01); *C12N 9/0006* (2013.01); *C12N 9/78* (2013.01); *C12N 9/93* (2013.01); *C12P 5/005* (2013.01); *C12P 5/026* (2013.01); *C12P 7/02* (2013.01); *C12P 7/04* (2013.01); *C12P 7/16* (2013.01); *C12P 7/42* (2013.01); *C12P 7/46* (2013.01); *C12P 13/001* (2013.01); *C12P 13/06* (2013.01); *C12P 13/08* (2013.01); *C12P 13/10* (2013.01); *C12P 17/10* (2013.01); *C12Y 101/01095* (2013.01); *C12Y 203/01054* (2013.01); *C12Y 305/04009* (2013.01); *C12Y 603/04003* (2013.01)

(58) Field of Classification Search
CPC ............ C12P 7/16; C12P 7/02; C12N 9/1029; C12Y 603/04003; C12Y 101/01095
See application file for complete search history.

(56) References Cited

U.S. PATENT DOCUMENTS

| | | | |
|---|---|---|---|
| 11,214,816 B2* | 1/2022 | Lee ..................... | C12P 7/625 |
| 2003/0124687 A1 | 7/2003 | Gunji et al. | |
| 2013/0196359 A1 | 8/2013 | Siegel et al. | |

FOREIGN PATENT DOCUMENTS

| | | |
|---|---|---|
| KR | 102000755 B1 | 7/2019 |
| WO | 2009062190 A2 | 5/2009 |

OTHER PUBLICATIONS

Federsel, C., et al., "A Well-Defined Iron Catalyst for the Reduction of Bicarbonates and Carbon Dioxide to Formates, Alkyl Formates, and Formamides", Angew. Chem. Int. Ed., 2010, pp. 9777-9780, vol. 49, Publisher: Wiley-bch Verleg GmbH & Co.

Gadgil, M., et al., "Transcriptional Response of *Escherichia coli* to Temperature Shift", Biotechnol. Prog., 2005, pp. 689-699, vol. 21, Publisher: American Chemical Society and American Institute of Chemical Engineers.

Gibson, D., et al., "Enzymatic assembly of DNA molecules up to several hundred kilobases", Nature Methods, 2009, pp. 343-345, vol. 6, No. 5, Publisher: 2009 Nature America, Inc. (npg).

Gleizer, S., et al., "Conversion of *Escherichia coli* to Generate All Biomass Carbon from CO2", Cell, 2019, pp. 1255-1263, vol. 179, Publisher: Elsevier Inc.

Kumar, B., et al., "Renewable and metal-free carbon nanofibre catalysts for carbon dioxide reduction", Nature Communications: www.nature.com/naturecommunications, 2013, p. 2819, vol. 4, No. DOI: 10.1038, Publisher: MacMillan Publishers Limited.

(Continued)

*Primary Examiner* — Tekchand Saidha
(74) *Attorney, Agent, or Firm* — Hultquist, PLLC; Steven J. Hultquist

(57) ABSTRACT

Disclosed is a recombinant microorganism capable of growing using only carbon dioxide and formic acid by introducing and improving a metabolic pathway for synthesizing pyruvic acid from carbon dioxide and formic acid to enhance pyruvic acid synthesis efficiency and performing additional genetic manipulation, and a method for producing useful substances using the same. Advantageously, the recombinant microorganism is capable of synthesizing pyruvic acid, a C3 organic compound, at a remarkably improved rate, and in particular, grows well even in a medium containing only carbon dioxide and formic acid as carbon sources without a glucose supply, and is thereby capable of synthesizing pyruvic acid and various high value-added compounds using the same as an intermediate product in an economically efficient manner.

20 Claims, 8 Drawing Sheets
Specification includes a Sequence Listing.

(56) References Cited

OTHER PUBLICATIONS

Neumann, E., et al., "Gene transfer into mouse lyoma cells by electroporation in high electric fields", The EMBO Journal, 1982, pp. 841-845, vol. 1, No. 7, Publisher: IRL Press Limited.

Schwander, T., et al., "A synthetic pathway for the fixation of carbon dioxide in vitro", Science, 2016, pp. 900-904, vol. 354, No. 6314, Publisher: sciencemag.org.

Studt, F., et al., "Discovery of a Ni—Ga catalyst for carbon dioxide reduction to methanol", Nature Chemistry, Mar. 2, 2014, pp. 320-324, vol. 6, No. Doi: 10.1038/NCHEM.1, Publisher: Macmillan Publishers Limited.

Zamboni, N., et al., "13 C-based metabolic flux analysis", Nature Protocols, 2009, pp. 878-892, vol. 4, No. 6.

Kim, S., et al., "Growth of *E. coli* on formate and methanol via the reductive glycine pathway", Nature Chemical Biology, 2020, pp. 538-545, vol. 16, Publisher: www.nature.com/naturechemicalbiology.

\* cited by examiner

[Fig. 1]
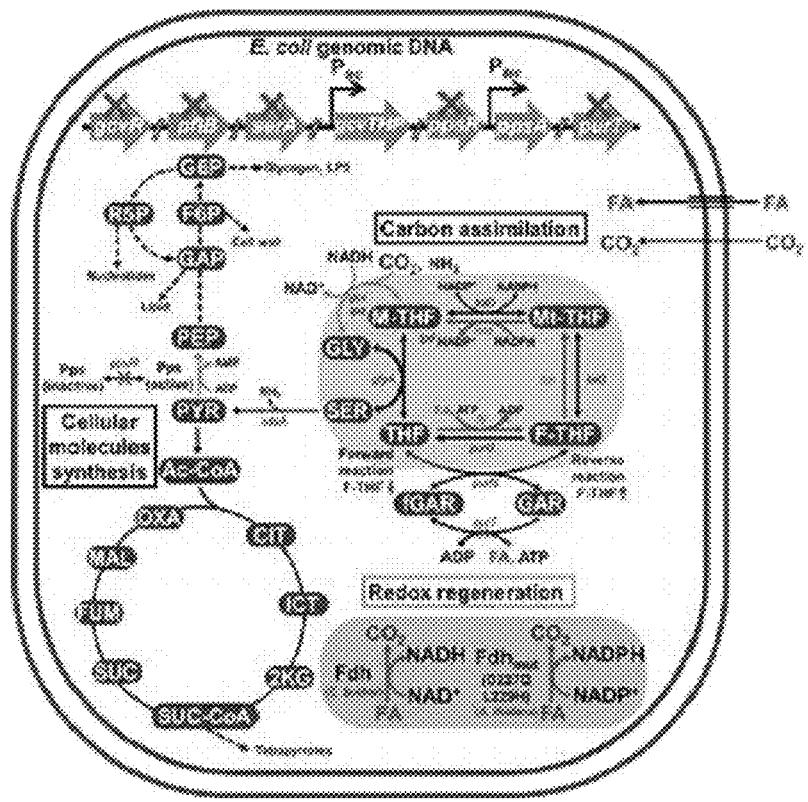
[Fig. 2]
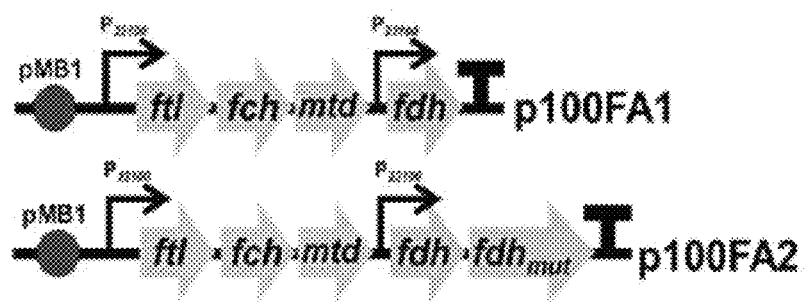

[Fig. 3]
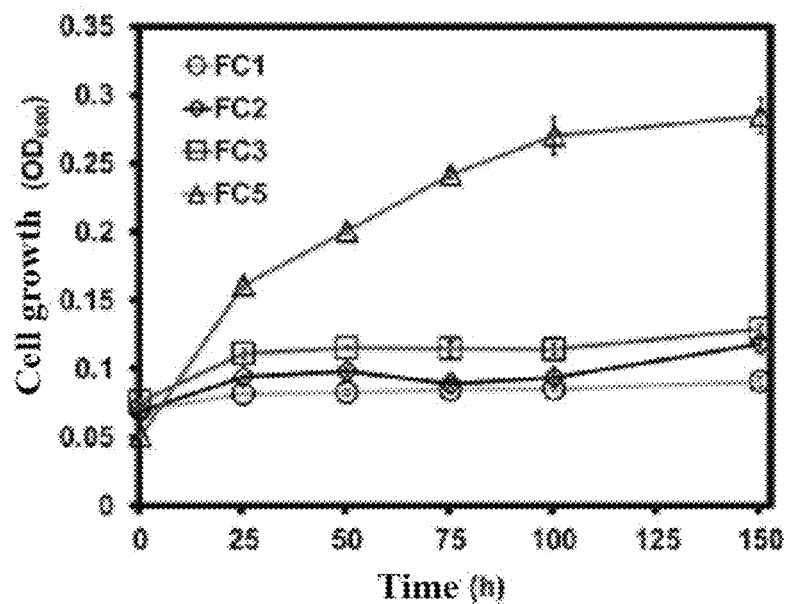
[Fig. 4]
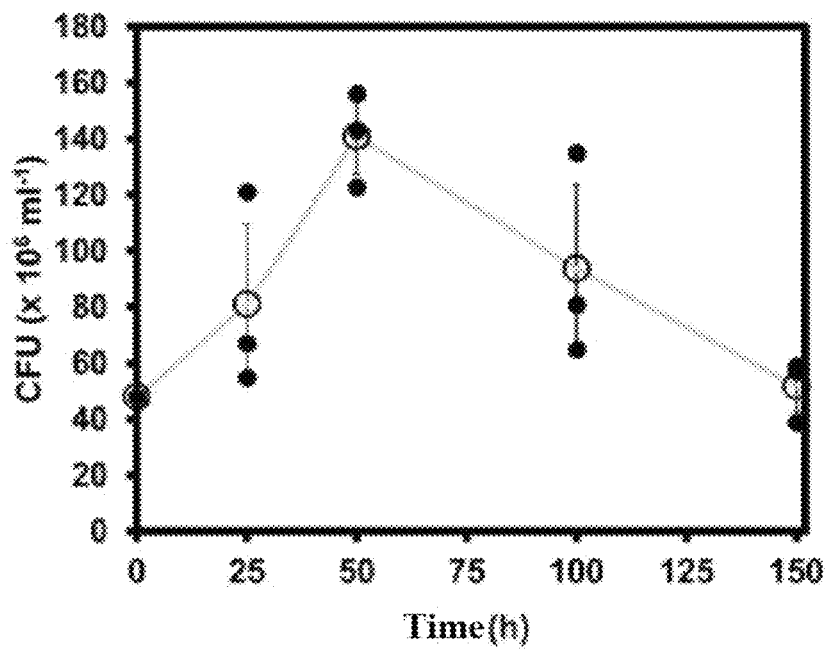

[Fig. 5]
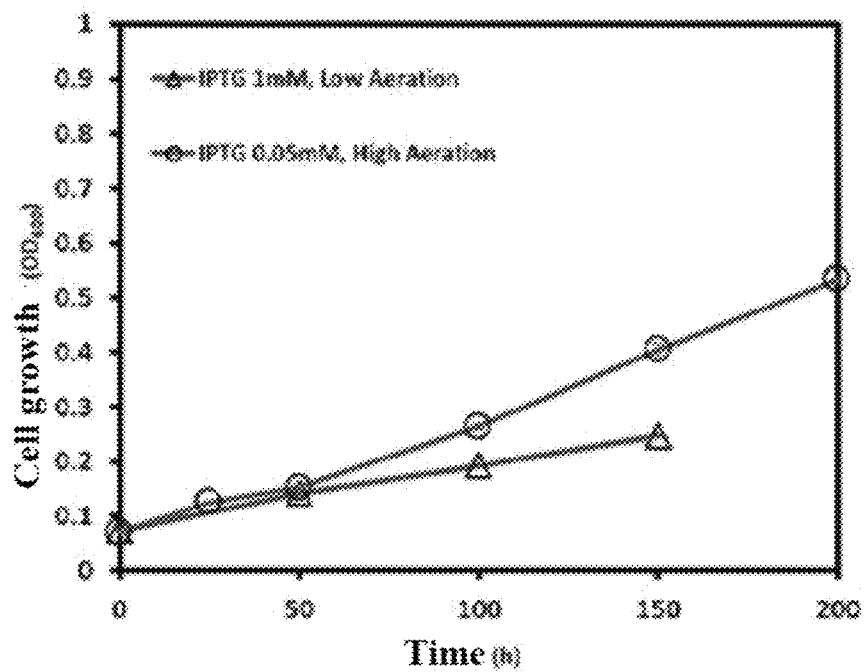
[Fig. 6]
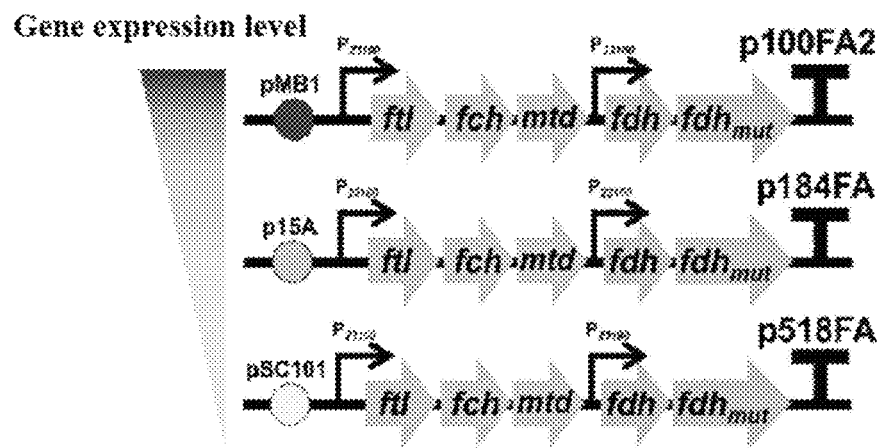

[Fig. 7]
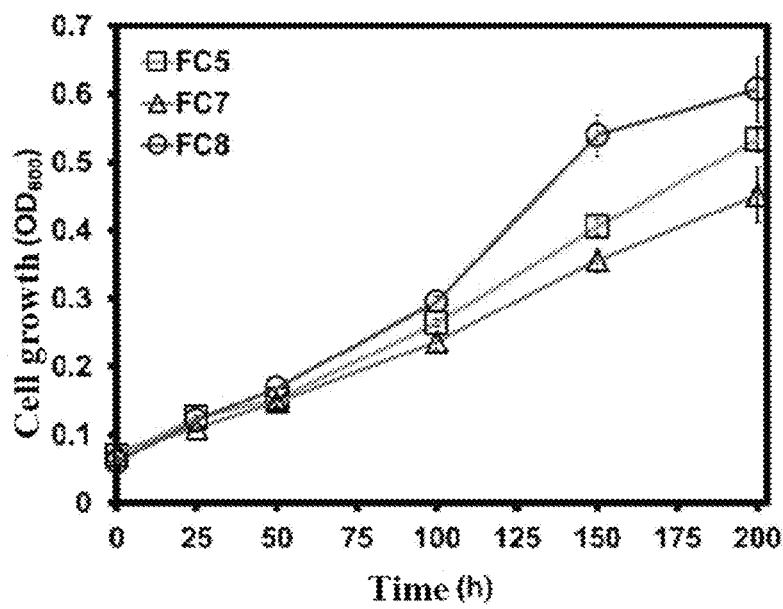
[Fig. 8]
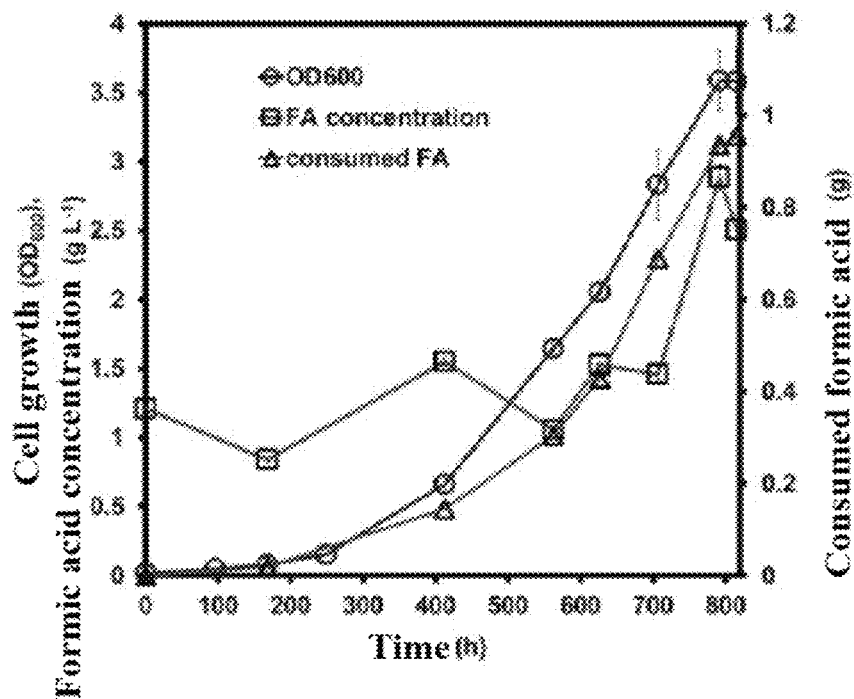

[Fig. 9]
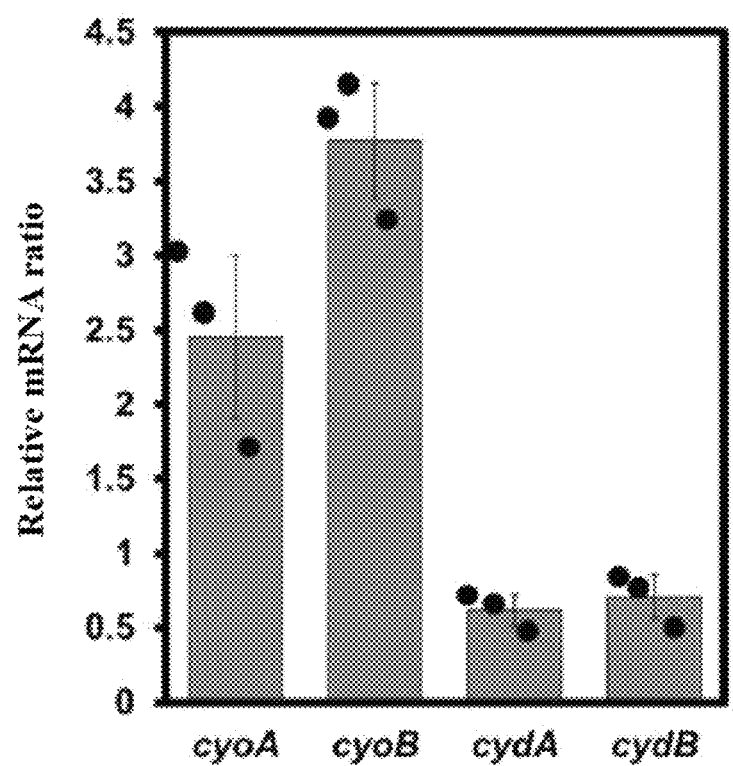

[Fig. 10]
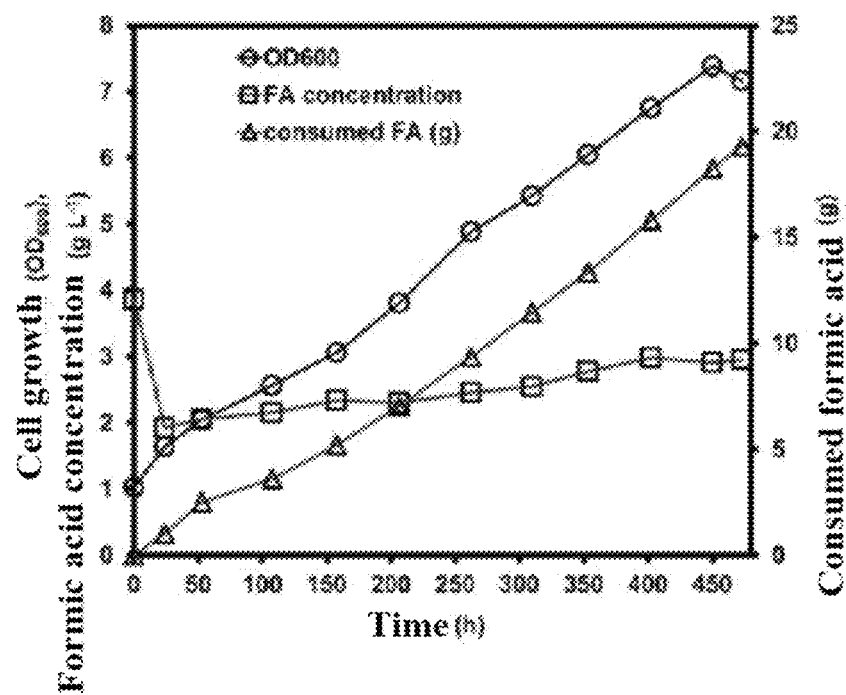
[Fig. 11]
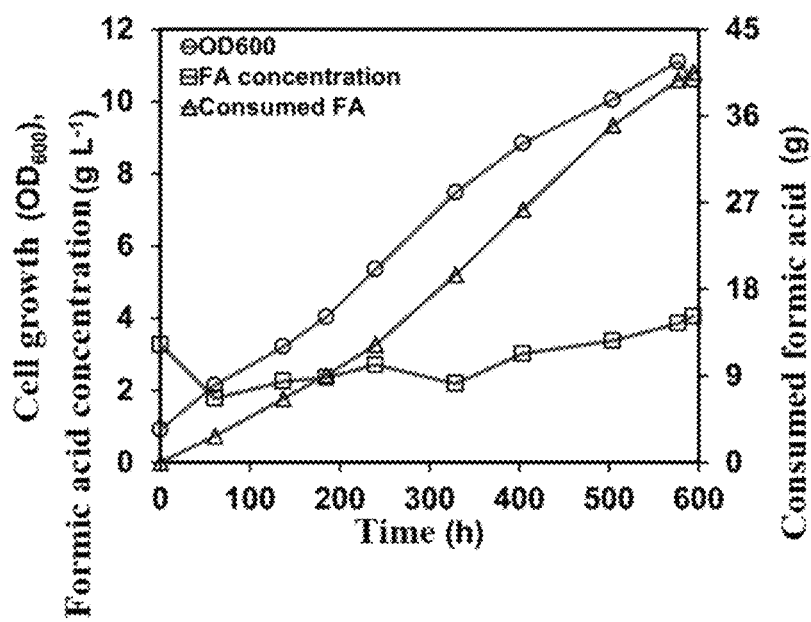

[Fig. 12]
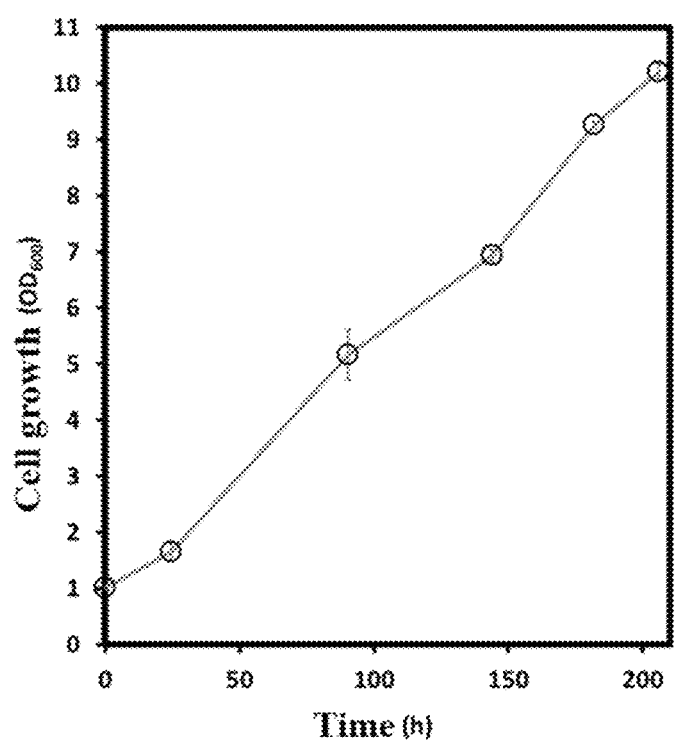

[Fig. 13]
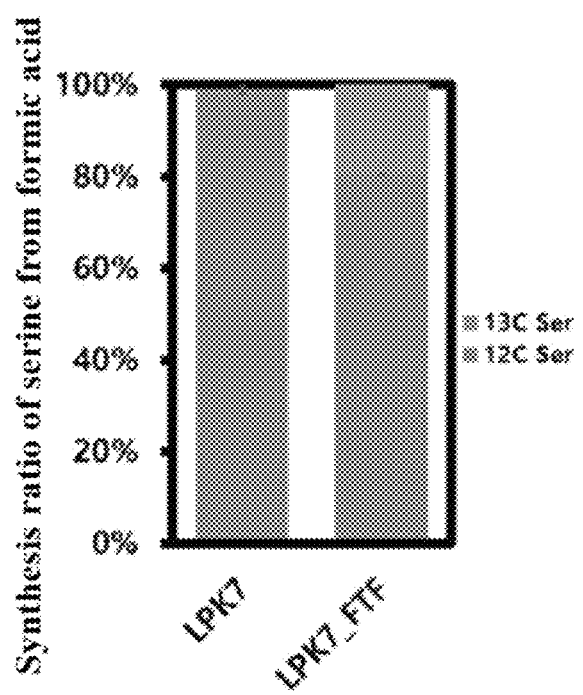

SEQUENCE LISTING

<160> NUMBER OF SEQ ID NOS: 39

<210> SEQ ID NO 1
<211> LENGTH: 1674
<212> TYPE: DNA
<213> ORGANISM: Artificial Sequence
<220> FEATURE:
<223> OTHER INFORMATION: Synthetic construct

<400> SEQUENCE: 1

```
atgccctcag atatcgagat cgcccgcgcg gcgaccctga agccgatcgc ccaggtcgcc      60
gaaaagctcg gcatcccgga cgaggcgctt cacaattacg gcaagcacat cgccaagatc     120
gaccacgact tcatcgcctc gctcgagggt aagcccgagg gcaagctggt gctcgtcacc     180
```

```
gcgatctcgc cgacgcctgc gggcgagggc aagaccacca cgactgtggg gctcggcgac      240
gcgctcaacc gcatcggcaa gcgggcggtg atgtgcctgc gcgagccctc gctcggcccc      300
tgcttcggca tgaagggcgg cgcggccggt ggcggcaagg cgcaggtcgt gccgatggag      360
cagatcaacc tgcacttcac cggcgacttc cacgccatca cctcggcgca ctcgctcgcc      420
gccgctctga tcgacaacca catctactgg gccaacgagc tcaacatcga cgtgcgccgc      480
atccactggc gccgcgtggt cgacatgaac gaccgagcgc tgcgcgcgat caaccagtcg      540
ctcggcggcg tcgccaacgg ctttccgcgt gaggacggct tcgacatcac cgtcgcctcc      600
gaggtgatgg cggtgttctg cctcgccaag aatctggctg acctcgaaga gcggctcggc      660
cgcatcgtca tcgccgagac ccgcgaccgc aagccggtga cgctggccga cgtgaaggcg      720
accggtgcga tgaccgttct cctcaaggac gcgcttcagc cgaacctcgt gcagacgctg      780
gagggcaacc cggccctgat ccatggcggc ccgttcgcca acatcgccca cggctgcaac      840
tcggtgatcg ccacccgcac cggcctgcgg ctggccgact acaccgtcac cgaggccggc      900
ttcgcgcgcg atctcggcgc ggagaagttc atcgacatca agtgccgcca gaccggcctc      960
aagccctcgt cggtggtgat cgtcgccacg atccgcgccc tcaagatgca tggcggcgtc     1020
aacaagaagg atctccaggc tgagaacctc gacgcgctgg agaagggctt cgccaacctc     1080
gagcgccacg tgaataacgt ccggagcttc ggcctgccgg tggtggtggg tgtgaaccac     1140
ttcttccagg acaccgacgc cgagcatgcc cggttgaagg agctgtgccg cgaccggctc     1200
caggtcgagg cgatcacctg caagcactgg cggagggcg gcgcgggcgc cgaggcgctg     1260
gcgcaggccg tggtgaagct cgccgagggc gagcagaagc cgctgacctt cgcctacgag     1320
accgagacga agatcaccga caagatcaag gcgatcgcga ccaagctcta cggcgcggcc     1380
gacatccaga tcgagtcgaa ggccgccacc aagctcgccg gcttcgagaa agacggctac     1440
ggcaaattgc cggtctgcat ggccaagacg cagtactcgt tctcgaccga cccgacccctg     1500 atgggcgcgc cctcgggcca cctcgtctcg gtgcgcgacg tgcgcctctc ggcgggcgcc     1560
ggcttcgtcg tggtgatctg cggtgagatc atgaccatgc cgggtctgcc aaaagtgccg     1620
gcggcggaca ccatccgcct ggacgccaac ggtcagatcg acgggctgtt ctag            1674
```

<210> SEQ ID NO 2
<211> LENGTH: 627
<212> TYPE: DNA
<213> ORGANISM: Artificial Sequence
<220> FEATURE:
<223> OTHER INFORMATION: Synthetic construct

<400> SEQUENCE: 2

```
atggccggca acgagacgat cgaaacattc ctcgacggcc tggcgagctc ggccccgacc       60
cccggcggcg gcggtgccgc gcgatctcc ggcgccatgg gcgcggcgct ggtgtcgatg       120
gtgtgcaacc tcaccatcgg caagaagaag tatgtcgagg tcgaggccga cctgaagcag      180
gtgctggaga agtcggaagg cctgcgccgc acgctcaccg gcatgatcgc cgacgacgtc      240
gaggctttcg acgcggtgat gggcgcctac gggctgccga agaacaccga cgaagagaag      300
gccgcccgcg ccgccaagat tcaagaggcg ctcaaaaccg cgaccgacgt gccgctcgcc      360
tgctgccgcg tctgccgcga ggtgatcgac ctggccgaga tcgtcgccga gaagggcaat      420
ctcaacgtca tctcggatgc cggcgtcgcc gtgctctcgg cctatgccgg cctgcgctcg      480
```

```
gcggccctta acgtctacgt caacgccaag ggcctcgacg accgcgcctt cgccgaggag    540
cggctgaagg agctggaggg cctactggcc gaggcgggcg cgctcaacga gcggatctac    600
gagaccgtga agtccaaggt aaactga                                        627
```

<210> SEQ ID NO 3
<211> LENGTH: 867
<212> TYPE: DNA
<213> ORGANISM: Artificial Sequence
<220> FEATURE:
<223> OTHER INFORMATION: Synthetic construct

<400> SEQUENCE: 3

```
atgtccaaga agctgctctt ccagttcgac accgatgcca cgccgagcgt cttcgacgtc     60
gtcgtcggct acgacggcgg tgccgaccac atcaccggct acgcaacgt cacgcccgac    120 aacgtcggcg cctatgtcga cggcacgatc tacacccgcg gcggcaagga aagcagtcg     180 acggcgatct tcgtcggcgg cggcgacatg gcggccggcg agcgggtgtt cgaggcggtg    240
aagaagcgct tcttcggccc gttccgcgtg tcctgcatgc tggattcgaa cggctccaac    300
acgaccgctg cggcgggcgt ggcgctcgtc gtcaaggcgg cgggcggctc ggtcaagggc    360
aagaaggccg tcgtgctcgc gggcaccggc ccggtcggca tgcgctcggc ggcgctgctt    420
gccggcgagg gcgccgaggt cgtgctgtgc gggcgcaagc tcgacaaggc gcaggccgcg    480
gccgattccg tgaacaagcg cttcaaggtg aacgtcaccg cggccgagac cgcggacgac    540
gcttcgcgtg ccgaggccgt gaagggcgcc catttcgtct tcaccgccgg tgcgatcggc    600
cttgaactgc tgccgcaggc agcctggcag aacgagagtt cgatcgagat cgtggccgac    660
tacaacgccc agccgccgct cggcatcggc gggatcgatg cgaccgacaa aggcaaggaa    720
tacggcggaa agcgcgcctt cggtgcgctc ggcatcggcg gcttgaagct caagctgcac    780
cgcgcctgca tcgccaagct gttcgagtcg agcgaaggcg tcttcgacgc cgaggagatc    840
tacaagctgg ccaaggaaat ggcctga                                        867
```

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4

```
cccgctcgcc aaggcttgaa ggaggaattc atgccctcag atatcgagat c              51
```

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5

```
ctagaacagc ccgtcgatc                                                  19
```

<210> SEQ ID NO 6
<211> LENGTH: 51
<212> TYPE: DNA
<213> ORGANISM: Artificial Sequence
<220> FEATURE:
<223> OTHER INFORMATION: Primer

```
<400> SEQUENCE: 6
gatcgacggg ctgttctaga ggaggaattc atggccggca acgagacgat c          51

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tcagtttacc ttggacttca c                                            21

<210> SEQ ID NO 8
<211> LENGTH: 53
<212> TYPE: DNA
<213> ORGANISM: Artificial Sequence
<220> FEATURE:
<223> OTHER INFORMATION: Primer

<400> SEQUENCE: 8
gtgaagtcca aggtaaactg aaggaggaat tcatgtccaa gaagctgctc ttc          53

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
tcatccgcca aaacagccaa gtcaggccat ttccttggcc                        40

<210> SEQ ID NO 10
<211> LENGTH: 1095
<212> TYPE: DNA
<213> ORGANISM: Artificial Sequence
<220> FEATURE:
<223> OTHER INFORMATION: Synthetic construct

<400> SEQUENCE: 10
atggcacaac agactccttt gtacgaacaa cacacgcttt gcggcgctcg catggtggat   60
ttccacggct ggatgatgcc gctgcattac ggttcgcaaa tcgacgaaca tcatgcggta  120
cgtaccgatg ccggaatgtt tgatgtgtca catatgacca tcgtcgatct tcgcggcagc  180
cgcacccggg agtttctgcg ttatctgctg cgaacgatg tggcgaagct caccaaaagc   240
ggcaaagccc tttactcggg gatgttgaat gcctctggcg gtgtgataga tgacctcatc  300
gtctactact ttactgaaga tttcttccgc ctcgttgtta actccgccac ccgcgaaaaa  360
gacctctcct ggattaccca acacgctgaa cctttcggca tcgaaattac cgttcgtgat  420
gacctttcca tgattgccgt gcaagggccg aatgcgcagg caaaagctgc cacactgttt  480
aatgacgccc agcgtcaggc ggtggaaggg atgaaaccgt tctttggcgt gcaggcgggc  540
gatctgttta ttgccaccac tggttatacc ggtgaagcgg gctatgaaat tgcgctgccc  600
aatgaaaaag cggccgattt ctggcgtgcg ctggtggaag cgggtgttaa gccatgtggc  660
ttgggcgcgc gtgacacgct gcgtctggaa gcgggcatga atctttatgg tcaggagatg  720
gacgaaacca tctctccttt agccgccaac atgggctgga ccatcgcctg gaaccggca   780 gatcgtgact ttatcggtcg tgaagccctg gaagtcagc gtgagcatgg tacagaaaaa  840
ctggttggtc tggtgatgac cgaaaaaggc gtgctgcgta tgaactgcc ggtacgcttt  900
```

```
accgatgcgc agggcaacca gcatgaaggc attatcacca gcggtacttt ctccccgacg    960
ctgggttaca gcattgcgct ggcgcgcgtg ccggaaggta ttggcgaaac ggcgattgtg   1020
caaattcgca accgtgaaat gccggttaaa gtgacaaaac ctgttttgt gcgtaacggc    1080 aaagccgtcg cgtga                                                    1095

<210> SEQ ID NO 11
<211> LENGTH: 390
<212> TYPE: DNA
<213> ORGANISM: Artificial Sequence
<220> FEATURE:
<223> OTHER INFORMATION: Synthetic construct

<400> SEQUENCE: 11
atgagcaacg taccagcaga actgaaatac agcaaagaac acgaatggct gcgtaaagaa     60
gccgacggca cttacaccgt tggtattacc gaacatgctc aggagctgtt aggcgatatg    120
gtgtttgttg acctgccgga agtgggcgca acggttagcg cgggcgatga ctgcgcggtt    180
gccgaatcgg taaaagcggc gtcagacatt tatgcgccag taagcggtga atcgtggcg     240 gtaaacgacg cactgagcga ttccccggaa ctggtgaaca gcgaaccgta tgcaggcggc    300
tggatcttta aaatcaaagc cagcgatgaa agcgaactgg aatcactgct ggatgcgacc    360
gcatacgaag cattgttaga agacgagtaa                                    390

<210> SEQ ID NO 12
<211> LENGTH: 2874
<212> TYPE: DNA
<213> ORGANISM: Artificial Sequence
<220> FEATURE:
<223> OTHER INFORMATION: Synthetic construct

<400> SEQUENCE: 12
atgacacaga cgttaagcca gcttgaaaac agcggcgctt ttattgaacg ccatatcgga     60
ccggacgccg cgcaacagca agaaatgctg aatgccgttg gtgcacaatc gttaaacgcg    120
ctgaccggcc agattgtgcc gaaagatatt caacttgcga caccaccgca ggttggcgca    180
ccggcgaccg aatacgccgc actggcagaa ctcaaggcta ttgccagtcg caataaacgc    240
ttcacgtctt acatcggcat gggttacacc gccgtgcagc taccgccggt tatcctgcgt    300
aacatgctgg aaaatccggg ctggtatacc gcgtacactc cgtatcaacc tgaagtctcc    360
cagggccgcc ttgaagcact gctcaacttc cagcaggtaa cgctggattt gactggactg    420
gatatggcct ctgcttctct tctggacgag gccaccgctg ccgccgaagc aatggcgatg    480
gcgaaacgcg tcagcaaact gaaaaatgcc aaccgcttct tcgtggcttc gatgtgcat     540 ccgcaaacgc tggatgtggt ccgtactcgt gccgaaacct ttggttttga agtgattgtc    600
gatgacgcgc aaaaagtgct cgaccatcag gacgtcttcg gcgtgctgtt acagcaggta    660
ggcactaccg gtgaaattca cgactacact gcgcttatta gcgaactgaa atcacgcaaa    720
attgtggtca gcgttgccgc cgatattatg gcgctggtgc tgttaactgc gccgggtaaa    780
cagggcgcgg atattgtttt tggttcggcg caacgcttcg gcgtgccgat gggctacggt    840
ggcccacacg cggcattctt tgcggcgaaa gatgaataca acgctcaat gccgggccgt    900 attatcggtg tatcgaaaga tgcagctggc aataccgcgc tgcgcatggc gatgcagact    960
cgcgagcaac atatccgccg tgagaaagcg aactccaaca tttgtacttc ccaggtactg    1020
ctggcaaaca tcgccagcct gtatgccgtt tatcacggcc cggttggcct gaaacgtatc    1080
```

| | | | |
|---|---|---|---|
| gctaaccgca | ttcaccgtct | gaccgatatc ctggcggcgg gcctgcaaca aaaaggtctg | 1140 |
| aaactgcgcc | atgcgcacta | tttcgacacc ttgtgtgtgg aagtggccga caaagcgggc | 1200 |
| gtactgacgc | gtgccgaagc | ggctgaaatc aacctgcgta gcgatattct gaacgcggtt | 1260 |
| gggatcaccc | ttgatgaaac | aaccacgcgt gaaaacgtaa tgcagctttt caacgtgctg | 1320 |
| ctgggcgata | ccacggcct | ggacatcgac acgctggaca agacgtggc tcacgacagc | 1380 |
| cgctctatcc | agcctgcgat | gctgcgcgac gacgaaatcc tcacccatcc ggtgtttaat | 1440 |
| cgctaccaca | gcgaaaccga | aatgatgcgc tatatgcact cgctggagcg taaagatctg | 1500 |
| gcgctgaatc | aggcgatgat | cccgctgggt tcctgcacca tgaaactgaa cgccgccgcc | 1560 |
| gagatgatcc | caatcacctg | gccggaattt gccgaactgc acccgttctg cccgccggag | 1620 |
| caggccgaag | gttatcagca | gatgattgcg cagctggctg actggctggt gaaactgacc | 1680 |
| ggttacgacg | ccgtttgtat | gcagccgaac tctggcgcac agggcgaata cgcgggcctg | 1740 |
| ctggcgattc | gtcattatca | tgaaagccgc aacgaagggc atcgcgatat ctgcctgatc | 1800 |
| ccggcttctg | cgcacggaac | taaccccgct tctgcacata tggcaggaat gcaggtggtg | 1860 |
| gttgtggcgt | gtgataaaaa | cggcaacatc gatctgactg atctgcgcgc gaaagcggaa | 1920 |
| caggcgggcg | ataacctctc | ctgtatcatg gtgacttatc cttctaccca cggcgtgtat | 1980 |
| gaagaaacga | tccgtgaagt | gtgtgaagtc gtgcatcagt tcggcggtca ggtttaccct | 2040 |
| gatgcgcga | acatgaacgc | ccaggttggc atcacctcgc cgggctttat tggtgcggac | 2100 |
| gtttcacacc | ttaacctaca | taaaactttc tgcattccgc acggcggtgg tggtccgggt | 2160 |
| atgggaccga | tcggcgtgaa | agcgcatttg gcaccgtttg taccgggtca tagcgtggtg | 2220 |
| caaatcgaag | gcatgttaac | ccgtcagggc gcggtttctg cggcaccgtt cggtagcgcc | 2280 |
| tctatcctgc | caatcagctg | gatgtacatc cgcatgatgg gcgcagaagg gctgaaaaaa | 2340 |
| gcaagccagg | tggcaatcct | caacgccaac tatattgcca gccgcctgca ggatgccttc | 2400 |
| ccggtgctgt | ataccggtcg | cgacggtcgc gtggcgcacg aatgtattct cgatattcgc | 2460 |
| ccgctgaaag | aagaaaccgg | catcagcgag ctggatattg ccaagcgcct gatcgactac | 2520 |
| ggtttccacg | cgccgacgat | gtcgttcccg gtggcgggta cgctgatggt tgaaccgact | 2580 |
| gaatctgaaa | gcaaagtgga | actggatcgc tttatcgacg cgatgctggc tatccgcgca | 2640 |
| gaaattgacc | aggtgaaagc | cggtgtctgg ccgctggaag ataacccgct ggtgaacgcg | 2700 |
| ccgcacattc | agagcgaact | ggtcgccgag tgggcgcatc cgtacagccg tgaagttgcg | 2760 |
| gtattcccgg | caggtgtggc | agacaaatac tggccgacag tgaaacgtct ggatgatgtt | 2820 |
| tacggcgacc | gtaacctgtt | ctgctcctgc gtaccgatta gcgaatacca gtaa | 2874 |

<210> SEQ ID NO 13
<211> LENGTH: 2283
<212> TYPE: DNA
<213> ORGANISM: Artificial Sequence
<220> FEATURE:
<223> OTHER INFORMATION: Synthetic construct

<400> SEQUENCE: 13

| | | | |
|---|---|---|---|
| atgtccgagc | ttaatgaaaa | gttagccaca gcctgggaag ttttaccaa aggtgactgg | 60 |
| cagaatgaag | taaacgtccg | tgacttcatt cagaaaaact acactccgta cgagggtgac | 120 |
| gagtccttcc | tggctggcgc | tactgaagcg accaccaccc tgtgggacaa agtaatggaa | 180 |
| ggcgttaaac | tggaaaaccg | cactcacgcg ccagttgact ttgacaccgc tgttgcttcc | 240 |
| accatcaccc | tcacgacgc | tggctacatc aacaagcagc ttgagaaaat cgttggtctg | 300 |

```
cagactgaag ctccgctgaa acgtgctctt atcccgttcg gtggtatcaa aatgatcgaa    360
ggttcctgca aagcgtacaa ccgcgaactg gatccgatga tcaaaaaaat cttcactgaa    420
taccgtaaaa ctcacaacca gggcgtgttc gacgtttaca ctccggacat cctgcgttgc    480
cgtaaatctg gtgttctgac cggtctgcca gatgcatatg gccgtggccg tatcatcggt    540
gactaccgtc gcgttgcgct gtacggtatc gactacctga tgaaagacaa actggcacag    600
ttcacttctc tgcaggctga tctggaaaac ggcgtaaacc tggaacagac tatccgtctg    660
cgcgaagaaa tcgctgaaca gcaccgcgct ctgggtcaga tgaaagaaat ggctgcgaaa    720
tacggctacg acatctctgg tccggctacc aacgctcagg aagctatcca gtggacttac    780
ttcggctacc tggctgctgt taagtctcag aacggtgctg caatgtcctt cggtcgtacc    840
tccaccttcc tggatgtgta catcgaacgt gacctgaaag ctggcaagat caccgaacaa    900
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg taccctggtt accaaaaaca gcttccgttt cctgaacacc   1080
ctgtacacca tgggtccgtc tccggaaccg aacatgacca ttctgtggtc tgaaaaactg   1140
ccgctgaact tcaagaaatt cgccgctaaa gtgtccatcg acacctcttc tctgcagtat   1200
gagaacgatg acctgatgcg tccggacttc aacaacgatg actacgctat gcttgctgc    1260 gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca gtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga agttaaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggaccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160
gaaaacccgg aaaatatcc gcagctgacc atccgtgtat ctggctacgc agtacgtttc   2220
aactcgctga ctaaagaaca gcagcaggac gttattactc gtaccttcac tcaatctatg   2280
taa                                                                 2283

<210> SEQ ID NO 14
<211> LENGTH: 1233
<212> TYPE: DNA
<213> ORGANISM: Artificial Sequence
<220> FEATURE:
<223> OTHER INFORMATION: Synthetic construct
```

<400> SEQUENCE: 14

```
atggcaaagg tatcgctgga gaaagacaag attaagtttc tgctggtaga aggcgtgcac    60
caaaaggcgc tggaaagcct tcgtgcagct ggttacacca acatcgaatt tcacaaaggc   120
gcgctggatg atgaacaatt aaaagaatcc atccgcgatg cccacttcat cggcctgcga   180
tcccgtaccc atctgactga agacgtgatc aacgccgcag aaaaactggt cgctattggc   240
tgtttctgta tcgaacaaa ccaggttgat ctggatgcgg cggcaaagcg cgggatcccg   300
gtatttaacg caccgttctc aaatacgcgc tctgttgcgg agctggtgat ggcgaactg   360
ctgctgctat tgcgcggcgt gccggaagcc aatgctaaag cgcaccgtgg cgtgtggaac   420
aaactggcgg cgggttcttt tgaagcgcgc ggcaaaaagc tgggtatcat cggctacggt   480
catattggta cgcaattggg cattctggct gaatcgctgg aatgtatgt ttacttttat   540
gatattgaaa ataaactgcc gctgggcaac gccactcagg tacagcatct ttctgacctg   600
ctgaatatga gcgatgtggt gagtctgcat gtaccagaga atccgtccac caaaaatatg   660
atgggcgcga agaaatttc actaatgaag cccggctcgc tgctgattaa tgcttcgcgc   720
ggtactgtgg tggatattcc ggcgctgtgt gatgcgctgg cgagcaaaca tctggcgggg   780
gcggcaatcg acgtattccc gacggaaccg gcgaccaata gcgatccatt tacctctccg   840
ctgtgtgaat cgacaacgt ccttctgacg ccacacattg gcggttcgac tcaggaagcg   900
caggagaata tcggcctgga agttgcgggt aaattgatca agtattctga caatggctca   960
acgctctctg cggtgaactt cccggaagtc tcgctgccac tgcacggtgg cgtcgtctg  1020
atgcacatcc acgaaaaccg tccgggcgtg ctaactgcgc tgaacaaaat cttcgccgag  1080
cagggcgtca acatcgccgc gcaatatctg caaacttccg cccagatggg ttatgtggtt  1140
attgatattg aagccgacga agacgttgcc gaaaaagcgc tgcaggcaat gaaagctatt  1200
ccgggtacca ttcgcgcccg tctgctgtac taa                               1233
```

<210> SEQ ID NO 15
<211> LENGTH: 573
<212> TYPE: DNA
<213> ORGANISM: Artificial Sequence
<220> FEATURE:
<223> OTHER INFORMATION: Synthetic construct

<400> SEQUENCE: 15

```
ttgacactgt catcgcaaca ttatctggtg atcactgcgt tgggtgccga tcgccctgga    60
attgtgaaca ccatcacccg tcatgtcagt agttgcggct gtaatattga agacagtcgc   120
ctggcgatgc tgggagaaga gttcacgttt attatgctgc tttccggttc atggaatgcc   180
attactctga ttgaatcaac gttaccgttg aaaggtgccg aactggatct tttaatcgtg   240
atgaagcgca cgacggcgcg tccgcgtccg ccaatgccag catctgtctg ggttcaggtc   300
gatgtggcag actccccgca tttaattgaa cgcttcacag cacttttcga cgcgcatcat   360
atgaacattg cggagctggt gtcgcgcacg caacctgctg aaaatgaacg ggctgcgcag   420
ttgcatattc agataaccgc ccacagcccc gcatctgcgg acgcagcaaa tattgagcaa   480
gcgttcaaag ccctatgtac agaactcaat gcacaaggca gtattaacgt cgtcaattat   540
tcccaacatg atgaacagga tggagttaag taa                               573
```

<210> SEQ ID NO 16
<211> LENGTH: 834
<212> TYPE: DNA

<213> ORGANISM: Artificial Sequence
<220> FEATURE:
<223> OTHER INFORMATION: Synthetic construct

<400> SEQUENCE: 16

| | | | | | |
|---|---|---|---|---|---|
| atggataatg | ctgttgatcg | ccacgttttt | tatatttctg | atggtacggc | aataactgcg | 60 |
| gaggtattag | gacacgcagt | aatgtcacaa | tttcccgtca | ctatcagcag | catcacgctg | 120 |
| ccgtttgtcg | aaaatgagag | ccgtgcacgg | gcagtgaagg | atcagattga | cgcaatttat | 180 |
| caccagacag | gcgtgcgccc | gctggtcttc | tactccatcg | tgttgccgga | gattcgcgcc | 240 |
| atcatcttgc | aaagtgaagg | cttttgccag | gatatcgttc | aggcgctggt | tgccccgcta | 300 |
| caacaagaga | tgaaactgga | tccaacgccg | attgctcatc | gtacccatgg | ccttaaccct | 360 |
| aataatctca | ataaatatga | tgcgcgcatt | gcggcgattg | attacaccct | cgcccacgat | 420 |
| gacggcattt | cgttgcgcaa | tctggaccag | gctcaggtga | tcctgctcgg | tgtttctcgc | 480 |
| tgtggtaaaa | cccccaccag | tctgtatctg | gcaatgcagt | ttggtatccg | cgcggcaaac | 540 |
| tacccctta | ttgccgacga | tatggataat | ctggtgctac | ccgcgtcgct | caaaccgctt | 600 |
| cagcataaat | tgttcggcct | gactatcgac | ccggaacgtc | tggcggcgat | tcgcgaggaa | 660 |
| cgtcgggaga | acagtcgcta | tgcctcgctt | cgtcagtgca | ggatggaagt | cgcggaagtg | 720 |
| gaagccttgt | accgtaaaaa | tcagatcccg | tggattaaca | gtaccaatta | ttcggtagaa | 780 |
| gagattgcca | ccaagatcct | cgatatcatg | ggccttagtc | gccgaatgta | ctag | 834 |

<210> SEQ ID NO 17
<211> LENGTH: 1179
<212> TYPE: DNA
<213> ORGANISM: Artificial Sequence
<220> FEATURE:
<223> OTHER INFORMATION: Synthetic construct

<400> SEQUENCE: 17

| | | | | | |
|---|---|---|---|---|---|
| atgacgttat | taggcactgc | gctgcgtccg | gcagcaactc | gcgtgatgtt | attaggctcc | 60 |
| ggtgaactgg | gtaaagaagt | ggcaatcgag | tgtcagcgtc | tcggcgtaga | ggtgattgcc | 120 |
| gtcgatcgct | atgccgacgc | accagccatg | catgtcgcgc | atcgctccca | tgtcattaat | 180 |
| atgcttgatg | gtgatgcatt | acgccgtgtg | gttgaactgg | aaaaaccaca | ttatatcgtg | 240 |
| ccggagatcg | aagctattgc | caccgatatg | ctgatccaac | ttgaagagga | aggactgaat | 300 |
| gttgtcccct | gcgctcgcgc | aacgaaatta | acgatgaatc | gcgagggtat | ccgtcgcctg | 360 |
| gcggcagaag | agctgcagct | gcccacttcc | acttatcgtt | ttgccgatag | cgaaagcctt | 420 |
| ttccgcgagg | cggttgctga | cattggctat | ccctgcattg | taaaaccggt | gatgagctct | 480 |
| tccggcaagg | ggcagacgtt | tattcgttct | gcagagcaac | ttgctcaggc | atggaagtac | 540 |
| gctcagcaag | gcggtcgcgc | cggagcgggc | gcgtaattg | ttgaaggcgt | cgttaagttt | 600 |
| gacttcgaaa | ttaccctgct | aaccgtcagc | gcggtggatg | gcgtccattt | ctgtgcacca | 660 |
| gtaggtcatc | gccaggaaga | tggcgactac | cgtgaatcct | ggcaaccaca | gcaaatgagc | 720 |
| ccgcttgccc | ttgaacgtgc | gcaggagatt | gcccgtaaag | tggtgctggc | actgggcggt | 780 |
| tatgggttgt | ttggtgtcga | gctatttgtc | tgtggtgatg | aggtgatttt | cagtgaggtc | 840 |
| tcccctcgtc | cacatgatac | cgggatggtg | acgttaattt | ctcaagatct | ctcagagttt | 900 |
| gccctgcatg | tacgtgcctt | cctcggactt | ccggttggcg | ggatccgtca | gtatggtcct | 960 |
| gcagcttctg | ccgttattct | gccacaactg | accagtcaga | atgtcacgtt | tgataatgtg | 1020 |
| cagaatgccg | taggcgcaga | tttgcagatt | cgtttatttg | gtaagccgga | aattgatggc | 1080 |

```
agccgtcgtc tgggggtggc actggctact gcagagagtg ttgttgacgc cattgaacgc    1140
gcgaagcacg ccgccggaca ggtaaaagta cagggttaa                           1179

<210> SEQ ID NO 18
<211> LENGTH: 1095
<212> TYPE: DNA
<213> ORGANISM: Artificial Sequence
<220> FEATURE:
<223> OTHER INFORMATION: Synthetic construct

<400> SEQUENCE: 18
atgaagatcg ttttagtctt atatgatgct ggtaagcacg ctgctgatga agaaaaatta     60
tatggttgta ctgaaaataa attaggtatt gctaattggt aaaagatca aggtcatgaa    120 ctaattacta cttctgataa agaaggtgaa acaagtgaat tggataaaca tatcccagat    180
gctgatatta tcatcaccac tcctttccat cctgcttata tcactaagga aagacttgac    240
aaggctaaga acttaaaatt agtcgttgtc gctggtgttg ttctgatca cattgattta     300 gattatatta atcaaacagg taagaaaatc tcagtcttgg aagttacagg ttctaatgtt    360
gtctctgttg ctgaacacgt tgtcatgacc atgcttgtct tggttagaaa tttcgttcca    420
gcacatgaac aaattattaa ccacgattgg gaggttgctg ctatcgctaa ggatgcttac    480
gatatcgaag gtaaaactat tgctaccatt ggtgctggta gaattggtta cagagtcttg    540
gaaagattac tccctttaa tccaaaagaa ttattatact acgattatca gctttacca    600 aaagaagctg aagaaaaagt tggtgctaga gagttgaaaa atattgaaga attagttgct    660
caagctgata tcgttacagt taatgctcca ttacacgcag gtacaaaagg tttaattaat    720
aaggaattat tatctaaatt taaaaaaggt gcttggttag tcaataccgc aagaggtgct    780
atttgtgttg ctgaagatgt tgcagcagct ttagaatctg gtcaattaag aggttacggt    840
ggtgatgttt ggttcccaca accagctcca aaggatcacc catggagaga tatgagaaat    900
aaatatggtg ctggtaatgc catgactcct cactactctg gtactacttt agatgctcaa    960
acaagatacg ctgaaggtac taaaaatatc ttggaatcat tctttactgg taaatttgat   1020
tacagaccac aagatattat cttattaaat ggtgaatacg ttactaaagc ttacggtaaa   1080
cacgataaga aataa                                                   1095

<210> SEQ ID NO 19
<211> LENGTH: 61
<212> TYPE: DNA
<213> ORGANISM: Artificial Sequence
<220> FEATURE:
<223> OTHER INFORMATION: Primer

<400> SEQUENCE: 19
attgtgagcg gataacaatt tcacacagga aacagaccat gaagatcgtt ttagtcttat     60
a                                                                    61

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
gtaccgagct cgaattccat ttatttctta tcgtgtttac                           40
```

<210> SEQ ID NO 21
<211> LENGTH: 1155
<212> TYPE: DNA
<213> ORGANISM: Artificial Sequence
<220> FEATURE:
<223> OTHER INFORMATION: Synthetic construct

<400> SEQUENCE: 21

```
atggcgatga gacaagccgc taaggcaacg atcagggcct gttcttcctc ttcttcttcg      60
ggttacttcg ctcgacgtca gtttaatgca tcttctggtg atagcaaaaa gattgtagga     120
gttttctaca aggccaacga atacgctacc aagaaccctc acttccttgg ctgcgtcgag     180
aatgccttag gaatccgtga ctggcttgaa tcccaaggac atcagtacat cgtcactgat     240
gacaaggaag gccctgattg cgaacttgag aaacatatcc cggatcttca cgtcctaatc     300
tccactccct tccacccggc gtatgtaact gctgaaagaa tcaagaaagc caaaaacttg     360
aagcttctcc tcacagctgg tattggctcg gatcatattg atctccaggc agctgcagct     420
gctggcctga cggttgctga agtcacggga agcaacgtgg tctcagtggc agaagatgag     480
ctcatgagaa tcttaatcct catgcgcaac ttcgtaccag gtacaaccca ggtcgtcaaa     540
ggcgagtgga acgtcgcggg cattgcgtac agagcttatg atcttgaagg gaagacgata     600
ggaaccgtgg gagctggaag aatcggaaag cttttgctgc agcggttgaa accattcggg     660
tgtaacttgt tgtaccatca aaggcatcag atggcaccag agctggagaa agagactgga     720
gctaagttcg ttgaggatct gaatgaaatg ctccctaaat gtgacgttat agtcatcaac     780
atgcctctca cggagaagac aagaggaatg ttcaacaaag agttgatagg gaaattgaag     840
aaaggcgttt tgatagtgaa caacgcaaga ggagccatca tggagaggca agcagtggtg     900
gatgcggtgg agagtggaca cattggaggg tacagcggga acgtttggga cccacagcca     960
gctcctaagg accatccatg gcgttacatg cctaaccagg ctatgacccc tcatacctcc    1020
ggcaccacca ttgacgctca gctacggtat cggcgcgggg cgaaagacat gttggagaga    1080
tacttcaagg gagaagactt ccctactgag aattacatcg tcaaggacgg tgaacttgct    1140
cctcagtacc ggtaa                                                     1155
```

<210> SEQ ID NO 22
<211> LENGTH: 51
<212> TYPE: DNA
<213> ORGANISM: Artificial Sequence
<220> FEATURE:
<223> OTHER INFORMATION: Primer

<400> SEQUENCE: 22

```
gtaaacacga taagaaataa aggaggaatt catggcgatg agacaagccg c              51
```

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23

```
tcatccgcca aaacagccaa gttaccggta ctgaggagca ag                        42
```

<210> SEQ ID NO 24
<211> LENGTH: 42
<212> TYPE: DNA
<213> ORGANISM: Artificial Sequence

```
<220> FEATURE:
<223> OTHER INFORMATION: Primer

<400> SEQUENCE: 24
tgctgaaaat aagtcgtcct ggatccacta gttctagagc gg                    42

<210> SEQ ID NO 25
<211> LENGTH: 43
<212> TYPE: DNA
<213> ORGANISM: Artificial Sequence
<220> FEATURE:
<223> OTHER INFORMATION: Primer

<400> SEQUENCE: 25
actatttacg aaagtctcgg gcttatcgat accgtcgacc tcg                   43

<210> SEQ ID NO 26
<211> LENGTH: 44
<212> TYPE: DNA
<213> ORGANISM: Artificial Sequence
<220> FEATURE:
<223> OTHER INFORMATION: Primer

<400> SEQUENCE: 26
tgctgaaaat aagtcgtcct gcacctcgct aacggattca ccac                  44

<210> SEQ ID NO 27
<211> LENGTH: 46
<212> TYPE: DNA
<213> ORGANISM: Artificial Sequence
<220> FEATURE:
<223> OTHER INFORMATION: Primer

<400> SEQUENCE: 27
actatttacg aaagtctcgg gaattacaac ttatatcgta tggggc                46

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tgcataaacc gacactggcg                                             20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ttaacctgct tgccgtgctc                                             20

<210> SEQ ID NO 30
<211> LENGTH: 20
<212> TYPE: DNA
<213> ORGANISM: Artificial Sequence
<220> FEATURE:
<223> OTHER INFORMATION: Primer
```

```
<400> SEQUENCE: 30
tggctgcgtt cgaaaaactg                                                20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acatcggcaa acaagtctgg                                                20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ttgcgcactt ccataacgtg                                                20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tgaaaccgaa cgctttaggc                                                20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ttacgcactg ggcatcattg                                                20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
atgcgttctt catgctgcac                                                20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
aactccattg caccacactg                                                20
```

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
aagaacaaag acgccagcac                                              20

<210> SEQ ID NO 38
<211> LENGTH: 47
<212> TYPE: DNA
<213> ORGANISM: Artificial Sequence
<220> FEATURE:
<223> OTHER INFORMATION: Primer

<400> SEQUENCE: 38
ttatcaactc tactggggag gaattcatgc cctcagatat cgagatc                47

<210> SEQ ID NO 39
<211> LENGTH: 40
<212> TYPE: DNA
<213> ORGANISM: Artificial Sequence
<220> FEATURE:
<223> OTHER INFORMATION: Primer

<400> SEQUENCE: 39
tctagaggat ccccgggtac ctcaggccat ttccttggcc                        40

RECOMBINANT MICROORGANISM CAPABLE OF GROWING USING ONLY CARBON DIOXIDE AND FORMIC ACID AND METHOD FOR PRODUCING USEFUL SUBSTANCES USING THE RECOMBINANT MICROORGANISM

CROSS-REFERENCE TO RELATED APPLICATION

The priority under 35 USC § 119 of Korean Patent Application 10-2020-0086811 filed Jul. 14, 2020 is hereby claimed. The disclosure of Korean Patent Application 10-2020-0086811 is hereby incorporated herein by reference, in its entirety, for all purposes.

REFERENCE TO SEQUENCE LISTING SUBMITTED VIA EFS-WEB

This application includes an electronically submitted sequence listing in .txt format. The .txt file contains a sequence listing entitled "568_SeqListing_ST25.txt" created on Jul. 1, 2021 and is 27,771 bytes in size. The sequence listing contained in this .txt file is part of the specification and is hereby incorporated by reference herein in its entirety.

BACKGROUND OF THE INVENTION

Field of the Invention

The present invention relates to a recombinant microorganism capable of growing using only carbon dioxide and formic acid and a method for producing useful substances using the recombinant microorganism. More specifically, the present invention relates to a recombinant microorganism which is capable of growing using only carbon dioxide and formic acid by introducing and enhancing the metabolic pathway for synthesizing pyruvic acid from carbon dioxide and formic acid to improve the efficiency of pyruvic acid synthesis and performing additional genetic manipulation, and a method for producing useful substances using the recombinant microorganism.

DESCRIPTION OF THE RELATED ART

In an attempt to establish measures to reduce greenhouse gas emissions, which are a major cause of rapid climate change, research is actively underway on the synthesis of a liquid or solid organic substance having a higher carbon number, rather than a gaseous compound consisting of one carbon, such as carbon dioxide, which is the main component of greenhouse gas. Research on the conversion of a compound consisting of one carbon (a C1 compound) can be roughly classified into chemical methods and biological methods. Among them, chemical methods are carried out using electrochemical reactions based on metal- and non-metal catalysts. Through such reactions, carbon dioxide is converted into a non-gaseous carbon compound such as methanol or formic acid, and examples of related research include conversion using a carbon nanotube catalyst (Kumar et al., Nat. Comm. 2819, 2013), conversion using an iron catalyst (Christopher et al., Angew. Chem. Int. Ed. 49:50, 9777-9780, 2010), conversion using an alloy catalyst (Studt et al., Nat. Chem., 6, 320-324, 2014) and the like. Conversion using these chemical methods has the advantage of a relatively high rate, but has a limitation in that the products obtained through the C1 compound conversion process are single-carbon substances such as formic acid and methanol, rather than useful compounds containing multiple carbon atoms.

Regarding biological conversion methods, research is underway with the goal of converting a gaseous C1 compound into a non-gaseous compound and converting a C1 compound into a useful compound consisting of several carbon atoms. In the former case, research has been conducted on the use of metabolic pathways present in nature and the improvement thereof (PCT/US2008/083056), designs of new metabolic pathways (Schwander et al., Science, 354: 6314, 900-904, 2016), and the like. Examples of the latter case include the production of useful compounds using methanol-assimilating microorganisms (US 2003/0124687 A1), the production of compounds having three carbon atoms from formic acid (US 2013/0196359 A1), and the like. However, this research has limitations in that it is difficult to identify the effects thereof in in-vivo conditions due to the low efficiency thereof and in that whether the function thereof is compatible with metabolic pathways in living organisms has not been verified.

Therefore, research to overcome the limitations of the biological C1 compound conversion process described above and to thereby develop an efficient C1 compound conversion process is being continually conducted in the industry. In particular, among C1 compounds, formic acid has advantages in that it is relatively less toxic to organisms than other C1 compounds and is advantageous for assimilation (anabolic) reactions compared to other C1 compounds in terms of reaction mechanics, and can be synthesized easily and rapidly from carbon dioxide through chemical methods. However, the genomic information of the genus *Methylobacterium*, which is a representative formic-acid-assimilating bacterium, was discovered only in 2009, that is to say, foundational research for application thereof has only been conducted relatively recently. Currently, theoretically demonstrated methods of converting C1 carbon sources into useful chemicals are being verified. A recent study has reported *E. coli* growth using only carbon dioxide and formic acid (Gleizer, S. et al. Cell 179, 1255-1263, 2019, Kim, S. et al. Nat. Chem. Biol. 1-8, 2020). However, there is a limitation in that the level of cell growth is remarkably low.

Therefore, in a previous study (Korean Patent NO. 10-2000755), the present inventors designed and verified a novel metabolic pathway for converting formic acid, which is a C1 compound, into a useful compound composed of several carbons, and conducted additional research on the development of microorganisms that grow using only carbon dioxide and formic acid as carbon sources using the same. As a result, the present inventors have found that microorganisms can be grown using only carbon dioxide and formic acid as carbon sources by deleting the gene encoding the enzyme phosphoribosylglycinamide formyltransferase from the genome of *E. coli*, enhancing the metabolic flow of gluconeogenesis, and introducing formate dehydrogenase derived from microorganisms of the genus *Candida* and a mutant gene of formate dehydrogenase derived from plants of the genus *Arabidopsis*. Further, the present inventors have found that the microorganisms can grow to a sufficiently high cell density to be applicable to the production of useful chemicals by regulating the expression levels of the gene expressing the reconstructed tetrahydrofolate metabolic cycle, the gene expressing formate dehydrogenase derived from the microorganism of the genus *Candida* and a formate dehydrogenase mutant derived from plants of the genus *Arabidopsis*, effectively regulating the expression level of membrane protein required for energy supply in microorganisms by changing the culture temperature conditions, developing a culture process of increasing aeration according to the growth of microorganisms, and developing a culture process of maintaining the concentration of formic acid in the culture medium at an optimal level. Based on these findings, the present invention has been completed.

RELATED ART DOCUMENT

Patent Documents (Patent Document 1) PCT/US2008/083056
(Patent Document 2) US 2003/0124687
(Patent Document 3) US 2013/0196359
(Patent Document 4) KR 10-2000755

Non-Patent Documents (Non-patent Document 1) Kumar et al., Nat. Comm, 2819, 2013
(Non-patent Document 2) Christopher et al., Angew. Chem. Int. Ed. 49:50, 9777-9780, 2010
(Non-patent Document 3) Studt et al., Nat. Chem, 6, 320-324, 2014
(Non-patent Document 4) Schwander et al., Science, 354: 6314. 900-904, 2016
(Non-patent Document 5) Gleizer, S. et al. Cell 179, 1255-1263, 2019
(Non-patent Document 6) Kim, S. et al. Nat. Chem. Biol. 1-8, 2020

SUMMARY OF THE INVENTION

Therefore, the present invention has been made in view of the above problems, and it is one object of the present invention to provide a recombinant microorganism having improved efficiency of synthesis of useful substances including C3 compounds from formic acid and carbon dioxide.

It is another object of the present invention to provide a method for producing useful substances including C3 compounds from formic acid and carbon dioxide using the recombinant microorganism.

In accordance with one aspect of the present invention, the above and other objects can be accomplished by the provision of is a recombinant microorganism, in which a gene encoding a glycine cleavage system transcriptional repressor, pyruvate formate lyase, or phosphoglycerate dehydrogenase is attenuated or deleted from a host microorganism having a formic acid assimilation pathway, a gene encoding an enzyme involved in a glycine cleavage system reaction is enhancely expressed in the host microorganism having the formic acid assimilation pathway, and a gene encoding formate-tetrahydrofolate ligase, methenyl tetrahydrofolate cyclohydrolase, or methylene-tetrahydrofolate dehydrogenase is introduced into the host microorganism having the formic acid assimilation pathway.

In accordance with another aspect of the present invention, provided is a method for producing a C3 compound including (a) a step of culturing the recombinant microorganism with formic acid and carbon dioxide as carbon sources to produce a C3 compound, and (b) a step of collecting the produced C3 compound.

In accordance with another aspect of the present invention, provided is a method for producing a useful compound using pyruvic acid as an intermediate product including (a) a step of culturing the recombinant microorganism with formic acid and carbon dioxide as carbon sources to produce a useful substance having a pyruvic acid as an intermediate product, and (b) a step of collecting the produced useful substance.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the core metabolic pathway for assimilating carbon dioxide and formic acid of recombinant microorganisms, and genes, enzymes, and metabolites involved therein;

FIG. 2 is a plasmid map produced by introducing the gene involved in assimilation of carbon dioxide and formic acid, a plasmid, into which formate dehydrogenase derived from Candida and Arabidopsis is inserted, and a mutant of formate dehydrogenase derived from the genus *Arabidopsis*;

FIG. 3 is a graph showing cell growth of produced strains of DH5α FC1 to DH5α FC5 when cultured only with carbon dioxide and formic acid;

FIG. 4 is a graph showing the amount of change in CFU over time of the DH5α FC5 strain;

FIG. 5 is a graph comparing cell growth according to optimization of culture conditions;

FIG. 6 shows a map of plasmids produced to have different plasmid copy numbers and changes in gene expression level according to the type of plasmid;

FIG. 7 is a graph showing cell growth of each of DH5α FC5, FC7 and FC8 strains cultured with only carbon dioxide and formic acid;

FIG. 8 is a graph showing cell growth of a DH5α FC8 strain upon flask culture using only carbon dioxide and formic acid;

FIG. 9 is a graph showing the relative expression levels of cyoA, cyoB, cydA, and cydB by the DH5α FC8 strain upon culture at 32° C. compared to 37° C.;

FIG. 10 is a graph showing cell growth of the DH5α FC8 strain in fermenter culture using only carbon dioxide and formic acid;

FIG. 11 is a graph showing cell growth of the DH5α FC8 strain in a fermenter culture using only carbon dioxide and formic acid;

FIG. 12 is a graph showing cell growth of the DH5α FC8 strain in a fermenter culture using only carbon dioxide and formic acid; and FIG. 13 is a graph showing formic acid-derived $^{13}C$ carbon detected in serine in the *Mannheimia* strain introduced with the formic acid assimilation metabolic pathway (LPK7_FTF) and the wild-type *Mannheimia* strain (LPK7).

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that the rate of conversion of carbon dioxide and formic acid to pyruvic acid can be remarkably increased by further improving a recombinant microorganism having a novel circulating metabolic pathway capable of synthesizing C3 compounds from formic acid and carbon dioxide conceived by the present inventors (KR Patent No. 10-2000755), in particular, that the recombinant microorganisms can be made able to grow using only carbon dioxide and formic acid, without the additional supply of glucose, which was conventionally supplied to grow recombinant microorganisms, and C3 compound synthesis efficiency can be remarkably improved compared to the related art by improving the fermentation process in which the recombinant microorganism can synthesize pyruvic acid as well.

In one aspect, the present invention is directed to a recombinant microorganism, in which a gene encoding a glycine cleavage system transcriptional repressor, pyruvate formate lyase, or phosphoglycerate dehydrogenase is attenuated or deleted from a host microorganism having a formic acid assimilation pathway, a gene encoding an enzyme involved in a glycine cleavage system reaction is enhancely expressed in the host microorganism having the formic acid assimilation pathway, and a gene encoding formate-tetrahydrofolate ligase, methenyl tetrahydrofolate cyclohydrolase, or methylene-tetrahydrofolate dehydrogenase is introduced into the host microorganism having the formic acid assimilation pathway.

According to the present invention, the formic acid carbon assimilation pathway is a cyclic pathway for assimilating carbon dioxide and formic acid into pyruvic acid, having three carbon atoms, in microorganisms. Genes, coenzymes and energy carriers involved in the formic acid assimilation pathway of *E. coli* are shown in FIG. 1.

According to the present invention, the formic acid assimilation pathway can be combined with the central carbon assimilation pathway to synthesize a carbon compound having three or more carbon atoms. The host microorganism: i) inherently has a central carbon assimilation pathway; or ii) has a central carbon assimilation pathway introduced thereinto.

According to the present invention, the host microorganism is selected from the group consisting of *Escherichia, Mannheimia, Rhodobacter* and *Methylobacterium* genera, but is not limited thereto.

According to the present invention, expression of the gene encoding the enzyme involved in the glycine cleavage system reaction may be enhanced by substituting a native promoter with a strong promoter, but the invention is not limited thereto.

According to the present invention, the strong promoter is selected from the group consisting of a trc promoter, a tac promoter, a T7 promoter, a lac promoter and a trp promoter, but is not limited thereto.

According to the present invention, the formate-tetrahydrofolate ligase, the methenyl tetrahydrofolate cyclohydrolase, and the ethylene-tetrahydrofolate dehydrogenase are derived from *Methylobacterium extorquens*, but the invention is not limited thereto. The gene encoding the formate-tetrahydrofolate ligase has a nucleotide sequence of SEQ ID NO: 1, the gene encoding the methenyl tetrahydrofolate cyclohydrolase has a nucleotide sequence of SEQ ID NO: 2, and the gene encoding the methylene-tetrahydrofolate dehydrogenase has a nucleotide sequence of SEQ ID NO: 3, but the present invention is not limited thereto.

According to the present invention, a gene encoding a phosphoenolpyruvate synthase regulatory protein or phosphoribosylglycinamide formyltransferase may be further attenuated or deleted in the recombinant microorganism, expression of a gene encoding phosphoenolpyruvate synthase or H$^+$-translocating NAD(P) transhydrogenase may be further enhanced in the recombinant microorganism, and a gene encoding formate dehydrogenase and/or a mutant thereof may be further introduced into the recombinant microorganism.

According to the present invention, expression of the gene encoding the phosphoenolpyruvate synthase (ppsA) and H$^+$-translocating NAD(P) transhydrogenase (pntAB) is enhanced by substituting a native promoter with a strong promoter, and the strong promoter is selected from the group consisting of a trc promoter, a tac promoter, a T7 promoter, a lac promoter and a trp promoter, but the present invention is not limited thereto.

According to the present invention, genes encoding one or more selected from the group consisting of formate-tetrahydrofolate ligase, methenyl tetrahydrofolate cyclohydrolase, methylene-tetrahydrofolate dehydrogenase, formate dehydrogenase, and formate dehydrogenase mutant are introduced by being cloned into a vector containing an origin of replication having 1 to 12 copies, preferably by being cloned into a vector including an origin of replication having 1 to 5 copies, but the invention is not limited thereto.

According to the present invention, the formate dehydrogenase may be derived from *Candida boidinii*, and the gene encoding the formate dehydrogenase mutant may be derived from *Arabidopsis thaliana*, but the present invention is not limited thereto.

According to the present invention, the gene encoding the formate dehydrogenase is represented by a nucleotide sequence of SEQ ID NO: 18 and the gene encoding the formate dehydrogenase mutant is represented by a nucleotide sequence of SEQ ID NO: 21, but the present invention is not limited thereto.

According to one aspect of the present invention, the native promoter was replaced with a strong promoter in order to enhance the gene encoding the enzyme involved in the glycine cleavage system reaction in the recombinant microorganism, and the gene encoding the glycine cleavage system transcriptional repressor was deleted in order to suppress the glycine cleavage system. Additionally, the gene encoding pyruvate formate lyase was deleted to prevent unnecessary conversion of pyruvic acid to formic acid and to improve the pyruvate formation flow. In addition, the gene encoding D-3-phosphoglycerate dehydrogenase is a gene essential for growth in M9 minimal medium containing glucose. When this gene is deleted, 5,10-CH$_2$-THF, which is necessary for biosynthesis of metabolites such as purine and methionine, can be produced only through the C1 compound assimilation pathway. For this reason, as the metabolic flow of the C1 compound assimilation pathway is enhanced, the strain growth is facilitated. Thus, the gene encoding D-3-phosphoglycerate dehydrogenase was deleted.

The recombinant microorganism according to the present invention is capable of producing a C3 compound using only formic acid and carbon dioxide as carbon sources.

The recombinant microorganism according to the present invention is also capable of growing using only formic acid and carbon dioxide as carbon sources.

The genes of the present invention may be altered in various ways in the coding region, so long as the amino acid sequence of the protein expressed from the coding region is not changed, and may be freely varied or modified so long as the expression of genes is not affected in a region excluding the coding region, and such varied or modified genes also fall within the scope of the present invention.

Therefore, the present invention also includes a polynucleotide having a nucleotide sequence substantially identical to the gene as well as a fragment of the gene. The term "substantially identical polynucleotide" means a gene encoding an enzyme having the same function as that used in the present invention, regardless of the homology of the sequence. The term "fragment of the gene" also means a gene encoding an enzyme having the same function as that used in the present invention, regardless of the length of the fragment.

In addition, the amino acid sequence of the protein, which is an expression product of the gene of the present invention, can be obtained from biological resources such as various microorganisms, so long as the titer and activity of the corresponding enzyme are not affected, and these biological resources also fall within the scope of the present invention.

Thus, the present invention also includes polypeptides having amino acid sequences substantially identical to the protein, and fragments of the polypeptides. The term "substantially identical polypeptide" means a protein having the same function as that used in the present invention, regardless of the homology of the amino acid sequence. The term "fragment of the polypeptide" also means a protein having the same function as that used in the present invention, regardless of the length of the fragment.

As used herein, the term "vector" means a DNA product containing a DNA sequence operably linked to a regulation sequence capable of expressing DNA in a suitable host, and may be a plasmid, a phage particle, or a simple potential genome insert. Once the vector is transformed into an appropriate host, it may replicate and function independently of the genome of the host, or may in some cases be integrated with the host genome. Since the plasmid is the most commonly used type of vector, the terms "plasmid" and "vector" are sometimes used interchangeably throughout the specification of the present invention. For the purpose of the present invention, a plasmid vector is preferably used. A typical plasmid vector that can be used for this purpose includes (a) a replication origin to efficiently conduct replication so as to include several to several hundred plasmid vectors per host cell, (b) an antibiotic resistance gene to screen a host cell transformed with the plasmid vector, and (C) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method. After ligation, the vector should be transformed into an appropriate host cell. Transformation can be easily carried out using a calcium chloride or electroporation method (Neumann, et al., EMBO J., 1: 841, 1982).

According to the present invention, "gene is attenuated (or inactivated)" means that expression of the gene is attenuated compared to the wild type, or that the function or activity of the protein encoded by the gene is attenuated compared to the wild type.

Expression vectors well-known in the art can be used as vectors for enhancing or overexpressing genes according to the present invention.

When a nucleotide sequence is aligned with another nucleotide sequence based on a functional relationship, it is said to be "operably linked" thereto. This may be gene(s) and regulatory sequence(s) linked in such a way so as to enable gene expression when a suitable molecule (e.g., a transcriptional activator protein) is linked to the regulatory sequence(s). For example, DNA for a pre-sequence or secretory leader is operably linked to DNA for a polypeptide when expressed as a pre-protein involved in secretion of the polypeptide, a promoter or enhancer is operably linked to a coding sequence when it affects the transcription of the sequence, a ribosome-binding site is operably linked to a coding sequence when it affects the transcription of the sequence, or a ribosome-binding site is operably linked to a coding sequence when positioned to facilitate translation. Generally, "operably linked" means that the linked DNA sequence is in contact therewith, or that a secretory leader is in contact therewith and is present in the reading frame. However, the enhancer need not be in contact. The linkage of these sequences is carried out by ligation (linkage) at a convenient restriction enzyme site. When no such site exists, a synthetic oligonucleotide adapter or a linker according to a conventional method is used. As is well known in the art, in order to increase the expression level of a transgene in a host cell, the gene should be operably linked to a transcriptional/translational expression regulation sequence that functions in a selected expression host. Preferably, the expression regulation sequence and the corresponding gene are included in one recombinant vector containing both a bacterial selection marker and a replication origin. When the host cell is a eukaryotic cell, the recombinant vector should further include a useful expression marker in the eukaryotic expression host.

The host cell transformed with the recombinant vector described above constitutes another aspect of the present invention. As used herein, the term "transformation" means introducing DNA into a host and making the DNA replicable using an extrachromosomal factor or chromosomal integration.

It should be understood that not all vectors function identically in expressing the DNA sequences of the present invention. Likewise, not all hosts function identically for the same expression system. However, those skilled in the art will be able to make appropriate selections from among a variety of vectors, expression regulation sequences, and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should be also considered.

In addition, the gene introduced in the present invention may be introduced into the genome of a host cell, and may exist as a chromosomal factor. It will be apparent to those skilled in the art that even insertion of the gene into the genome of the host cell has the same effect as introducing the recombinant vector into the host cell.

Meanwhile, it was found in the present invention that the growth of the recombinant microorganism can be improved to 7-11 times by adjusting the dose of IPTG, culture temperature, aeration, and formic acid concentration and pH conditions in the step of culturing the recombinant microorganism.

In another aspect, the present invention is directed to a method for producing a C3 compound including: (a) a step of culturing the recombinant microorganism with formic acid and carbon dioxide as carbon sources to produce a C3 compound; and (b) a step of collecting the produced C3 compound.

According to the present invention, 0.02 to 0.08 mM IPTG, preferably 0.04 to 0.06 mM IPTG, most preferably 0.05 mM IPTG, is added in the step of culturing the recombinant microorganism. This induces gene expression using a remarkably attenuated dose of IPTG compared to the related art, in which 1 mM IPTG is used. This can enhance the growth of microorganisms while finely controlling the pyruvic acid synthesis metabolic pathway using carbon dioxide and formic acid.

According to the present invention, the recombinant microorganism may be cultured at 31 to 33° C., preferably at 32° C., but is not limited thereto. Under the temperature conditions as above, cytochrome bo3 ubiquinol oxidase (Cyo) and cytochrome bd-I ubiquinol oxidase (Cyd) most efficiently convert the reducing power into cellular energy, namely ATP.

According to the present invention, during the culturing step, the formic acid is maintained at a concentration of 2 to 3 g/l, and the pH is maintained at 6.6 to 7.0, but the present invention is not limited thereto. In addition, in the present invention, the recombinant microorganism may be initially cultured at a stirring speed of 450 to 550 rpm, and may then be cultured while increasing the stirring speed to a final speed of 700 to 800 rpm, but the present invention is not limited thereto. By supplying such a formic acid concentration, pH, and aeration, the growth rate of the recombinant microorganism according to the present invention is remarkably improved.

In another aspect, the present invention is directed to a method for producing a useful compound using pyruvic acid as an intermediate product including: (a) a step of culturing the recombinant microorganism with formic acid and carbon dioxide as carbon sources to produce a useful substance having a pyruvic acid as an intermediate product; and (b) a step of collecting the produced useful substance.

According to the present invention, the useful substance is selected from the group consisting of butanol, isobutanol, hexanol, heptanol, octanol, nonanol, decanol, tert-butanol, 1-pentanol, 2-pentanol, 3-pentanol, 2-methyl-1-butanol, 3-methyl-1-butanol, 2-methyl-2-butanol, isobutanol, putrescine, L-ornithine, arginine, polycyclic aromatic hydrocarbons (PAHs), polylactate, polylactate-co-glycolate, polyisovalerate, polyhydroxybutyrate (PHB), 4-hydroxybutyrate, biodiesel, gasoline, olefin, 5-aminovaleric acid, gamma-iminobutyric acid, 3-hydroxypyropionic acid, 3-aminopropionic acid, acrylic acid, 1,3-diaminopropane, caprolactam, threonine, valine, isoleucine, fumaric acid, malic acid, succinic acid, ceramide, astaxanthin, silybin, lycopene, lutein, and retinol, but is not limited thereto.

The recombinant microorganism and the method for producing a C3 compound using the same according to the present invention have the following characteristics.

First, the recombinant microorganism according to the present invention improves the rate of conversion of carbon dioxide and formic acid to pyruvic acid through improvement of the metabolically engineered strain. For example, the pflB gene and the serA gene were further deleted from the recombinant microorganism capable of synthesizing pyruvic acid using carbon dioxide and formic acid, firstly developed by the present inventors, to develop a strain capable of synthesizing pyruvic acid from carbon dioxide and formic acid at an improved rate (DH5α RG5). This strain synthesizes pyruvic acid from carbon dioxide and formic acid at a rate corresponding to 12.9% of the rate of synthesizing pyruvic acid from glucose, which is increased to 70% compared to the conventional recombinant microorganisms capable of synthesizing pyruvic acid from carbon dioxide and formic acid, developed by the present inventors.

The recombinant microorganism according to the present invention can be grown using only carbon dioxide and formic acid. The recombinant microorganisms previously developed by the present inventors are capable of producing pyruvic acid using carbon dioxide and formic acid, but glucose needs to be separately supplied for the growth of the recombinant microorganisms. However, the recombinant microorganism according to the present invention can grow using only carbon dioxide and formic acid without the supply of glucose by deleting the ppsR gene and the purT gene from the genome of the recombinant microorganism (DH5α RG5) having an improved rate of synthesis of pyruvic acid from the carbon dioxide and formic acid, substituting the native promoter of the ppsA gene with the strong trc promoter, and further introducing the formate dehydrogenase gene derived from *Candida boidinii* and the mutant gene of formate dehydrogenase derived from *Arabidopsis thaliana* through the plasmid.

According to the present invention, in order to further improve the growth rate of the recombinant microorganism (DH5α FC5), a recombinant microorganism (DH5α FC8) in which the number of copies of the introduced plasmid is further adjusted was developed. As a result, the growth rate of the recombinant microorganism DH5α FC8 was increased to a 1.14 times that of the recombinant microorganism DH5α FC5. According to the present invention, in order to further improve the growth rate of the recombinant microorganism (DH5α FC8), a recombinant microorganism (DH5α FC9) in which the native promoter of the pntAB gene was replaced with a strong trc promoter was developed. As a result, the growth rate of the recombinant microorganism DH5α FC9 was doubled compared to that of the recombinant microorganism DH5α FC8.

According to the present invention, culture and fermentation conditions that can maximize the growth of the recombinant microorganism were determined. The culture and fermentation conditions provide the maximum growth limit, $OD_{600}$=7.38-11.1, which is 7-11 times higher than the maximum growth limit, $OD_{600}$ (about 1), of *E. coli* grown using only carbon dioxide and formic acid previously reported in the literature (Kim, S. et al. Nat. Chem. Biol. 1-8, 2020), which was achieved by reducing the dose of IPTG for gene expression, decreasing the culture temperature, improving aeration, and controlling the formic acid concentration and pH.

EXAMPLE

Hereinafter, the present invention will be described in more detail with reference to the following examples. However, it will be obvious to those skilled in the art that the following examples are provided only for illustration of the present invention and should not be construed as limiting the scope of the present invention.

Example 1: Improvement in Metabolic Flow for Formation of Pyruvic Acid from Carbon Dioxide and Formic Acid Through Establishment of Carbon Dioxide and Formic Acid Assimilation Pathway and Metabolic Engineering Strategy In order to improve the carbon assimilation metabolic flow in the carbon dioxide and formic acid assimilation metabolic pathway, a plasmid containing the genes ftl, fch, and mtd involved in the carbon dioxide and formic acid assimilation pathway was introduced into a recombinant *E. coli* strain in which the gcvR, pflB and serA genes of *E. coli* were deleted and the gcvT promoter was replaced with the strong trc promoter to develop a recombinant strain that synthesizes 12.9% of the total pyruvic acid from carbon dioxide and formic acid.

Specifically, the foreign gene fragments required for plasmid production were prepared by conducting PCR using the genomic DNA of microorganisms having the corresponding gene as a template and using a primer designed for amplification of the gene and then collecting and purifying the amplified gene fragments, and the corresponding genes and primer sequences are shown in Tables 1 and 2 below.

TABLE 1

| Target gene | NCBI information | Derived microorganism |
|---|---|---|
| ftfL | Formate-tetrahydrofolate ligase CP001298 REGION: 434499-436172 [SEQ ID NO: 01] | *Methylobacterium extorquens* CM4 |
| fch | Methenyl tetrahydrofolate cyclohydrolase CP001298 REGION: 2231946-2232572 [SEQ ID NO: 02] | *Methylobacterium extorquens* CM4 |
| mtdA | Methylene-tetrahydrofolate dehydrogenase CP001298 REGION: 2230986-2231852 [SEQ ID NO: 03] | *Methylobacterium extorquens* CM4 |

[TABLE 2]

| Target gene | Primer sequence |
|---|---|
| ftfL [SEQ ID NO: 01] | [SEQ ID NO: 04]: 5'-CCCGCTCGCCAAGGCTTGA AGGAGGAATTCATGCCCTCAGA TATCGAGATC-3' [SEQ ID NO: 05]: 5'-CTAGAACAGCCCGTCGAT C-3' |
| fch [SEQ ID NO: 02] | [SEQ ID NO: 06]: 5'-GATCGACGGGCTGTTCTAG AGGAGGAATTCATGGCCGGCAA CGAGACGATC-3' [SEQ ID NO: 07]: 5'-TCAGTTTACCTTGGACTT CAC-3' |
| mtdA [SEQ ID NO: 03] | SEQ ID NO: 08]: 5'-GTGAAGTCCAAGGTAAACT GAAGGAGGAATTCATGTCCAAG AAGCTGCTCTTC-3' [SEQ ID NO: 09]: 5'-TCATCCGCCAAAACAGCC AAGTCAGGCCATTTCCTTGGC C-3' |

A plasmid containing genes encoding the above enzymes was produced to construct the carbon dioxide and formic acid assimilation pathway.

TABLE 3

| Plasmid | Characteristics |
|---|---|
| p100THF | Includes pBR322 replication origin, ampicillin resistance gene, BBa_23100 synthetic promoter, SEQ ID NO: 01 formate-tetrahydrofolate ligase, SEQ ID NO: 02 methenyl tetrahydrofolate cyclohydrolase, and SEQ ID NO: 03 methylene-tetrahydrofolate dehydrogenase |

Plasmids were produced from the plasmid backbone gene fragments and amplified gene fragments using the Gibson assembly method (Gibson et al., *Nat. Methods*, 6:5, 343-345, 2009), which is commonly used for the assembly of gene fragments, and each plasmid was produced to include one or more of the foreign genes set forth in Table above.

The recombinant plasmid produced by the method described above was transformed into *E. coli* to produce recombinant *E. coli*. The *E. coli* used in the present invention was *E. coli* DH5α (Invitrogen, USA), and transformation into *E. coli* was carried out using a chemical transformation method commonly used in the art.

Further, the native promoter was replaced with a strong trc promoter in order to enhance the gcvTHP gene (gcvT, NCBI GeneID: 947390; gcvH, NCBI GeneID: 947393; gcvP, NCBI GeneID: 947394) encoding the enzyme involved in the glycine cleavage system reaction in the recombinant microorganism, and the gene gcvR that suppresses the glycine cleavage system was deleted. Additionally, the gene pflB encoding pyruvate formate lyase was deleted to prevent unnecessary conversion of pyruvic acid to formic acid and to improve the pyruvate formation flow. In addition, the gene serA encoding D-3-phosphoglycerate dehydrogenase is a gene essential for growth in M9 minimal medium containing glucose. When this gene is deleted, $5,10-CH_2-THF$, which is necessary for biosynthesis of metabolites such as purine and methionine, can be produced only through the C1 compound assimilation pathway. Thus, as the metabolic flow of the C1 compound assimilation pathway is enhanced, the strain growth is facilitated. For this reason, the gene serA was deleted. The enhanced and deleted genes are given below.

TABLE 4

| Target gene | NCBI information | Derived microorganism |
|---|---|---|
| gcvT | Aminomethyltransferase NCBI GeneID: 947390 [SEQ ID NO: 10] | *Escherichia coli* |
| gcvH | Glycine cleavage system H protein NCBI GeneID: 947393 [SEQ ID NO: 11] | *Escherichia coli* |
| gcvP | Glycine decarboxylase NCBI Gene ID: 947394 [SEQ ID NO: 12] | *Escherichia coli* |
| pflB | Pyruvate formate lyase NCBI Gene ID: 945514 [SEQ ID NO: 13] | *Escherichia coli* |
| serA | Phosphoglycerate dehydrogenase NCBI Gene ID: 945258 [SEQ ID NO: 14] | *Escherichia coli* |
| gcvR | Glycine cleavage system transcriptional repressor Gene ID: 946950 [SEQ ID NO: 15] | *Escherichia coli* |

TABLE 5

| Strain name | Type of gene |
|---|---|
| DH5α GTPS | DH5α strain where gcvR, pflB and serA genes were deleted and native promoter of gcvT was changed to trc promoter |

The p100THF plasmid was introduced into the produced strain to produce the following strain.

TABLE 6

| DH5α RG5 | DH5α_GTPS harboring p100THF |
|---|---|

Carbon isotope analysis was performed on the recombinant *E. coli* (DH5α RG5) as an experimental group and wild-type *E. coli* (DH5α WT) as a control group to identify the increased metabolic flow for carbon dioxide and formic acid assimilation in the produced recombinant *E. coli* (DH5α RG5).

TABLE 7

| Ingredient | Content (g/l) |
| --- | --- |
| $Na_2HPO_4$ | 3.6 |
| $KH_2PO_4$ | 3 |
| NaCl | 0.5 |
| $NH_4Cl$ | 1 |
| $MgSO_4$ | 0.24 |
| $CaCl_2$ | 0.011 |
| Glucose | 5 |
| Sodium formate $^{13}C$ | 2.76 |
| Folate | 0.01 |
| Sodium bicarbonate $^{13}C$ | 3.4 |
| $FeSO_4$ | 0.00455 |
| $NiSO_4$ | 0.00464 |
| Sodium molybdate | 0.00618 |
| Thiamine | 0.01 |

The control and experimental *E. coli* were cultured in M9 medium containing formate and bicarbonate ions labeled with a $^{13}C$ carbon isotope (see the composition shown in Table 7 above), and then the *E. coli* cell samples were analyzed. Analysis of the mass number of amino acid constituting *E. coli* using *E. coli* cell samples was carried out using gas-chromatography/mass spectroscopy after hydrolysis of all of the proteins constituting *Escherichia coli* under strongly acidic and high-temperature conditions (Zamboni et al., *Nat. protocols*, 4:6, 878-892, 2009).

The result of isotope analysis showed that the DH5α RG5 strain increased the metabolic flow for the formation of pyruvic acid through assimilation with carbon dioxide and formic acid to 12.9% of the total metabolic flow for the formation of pyruvic acid.

Example 2: Development of Recombinant Microorganisms Capable of Growing Using Only Carbon Dioxide and Formic Acid Through Improvement of Metabolically Engineered Strain The ppsR and purT genes were deleted from the genome of the recombinant *E. coli* strain produced in Example 1, the promoter of the ppsA gene was replaced with a strong trc promoter to produce a recombinant *E. coli* strain (DH5α AKO1), and a plasmid (p100FA2), produced by adding the fdh gene and the fdhmut gene to the plasmid produced in Example 1, was introduced into the recombinant *E. coli* strain (DH5α AKO1) to produce *E. coli* (DH5α FC5) capable of growing using only carbon dioxide and formic acid.

TABLE 8

| Target gene | NCBI information | Derived microorganism |
| --- | --- | --- |
| ppsR | Phosphoenolpyruvate synthase regulatory protein NCBI GeneID: 946207 [SEQ ID NO: 16] | *Escherichia coli* |
| purT | Phosphoribosylglycinamide formyltransferase NCBI GeneID: 946368 [SEQ ID NO: 17] | *Escherichia coli* |

TABLE 9

| Plasmid | Characteristics |
| --- | --- |
| p100FA2 | Includes pBR322 replication origin, ampicillin resistance gene, BBa_23100 synthetic promoter, SEQ ID NO: 01 formate-tetrahydrofolate ligase, SEQ ID NO: 02 methenyl tetrahydrofolate cyclohydrolase, SEQ ID NO: 03 methylene-tetrahydrofolate dehydrogenase, SEQ ID NO: 18 formate dehydrogenase, and SEQ ID NO: 21 formate dehydrogenase mutant |

In order for cells to grow using only carbon dioxide and formic acid without glucose, uninterrupted supply of energy and reducing (redox) power is essential. For this purpose, a metabolic pathway for generating NADH and NADPH while converting formic acid into carbon dioxide is required. Therefore, the *Candida boidinii*-derived fdh gene encoding formate dehydrogenase using NAD+ and a mutant $fdh_{mut}$ of the *Arabidopsis thaliana*-derived fdh gene encoding formate dehydrogenase using NADP+ were introduced into the p100THF plasmid to construct a p100FA2 plasmid.

TABLE 10

| plasmid | Characteristics |
| --- | --- |
| p100FA2 | Includes pBR322 replication origin, ampicillin resistance gene, BBa_23100 synthetic promoter, SEQ ID NO: 01 formate-tetrahydrofolate ligase, SEQ ID NO: 02 methenyl tetrahydrofolate cyclohydrolase, SEQ ID NO: 03 methylene-tetrahydrofolate dehydrogenase, SEQ ID NO: 18 formate dehydrogenase, and SEQ ID NO: 21 formate dehydrogenase mutant |

TABLE 11

| Target gene | NCBI information | Derived microorganism |
| --- | --- | --- |
| fdh | Formate dehydrogenase EC: 1.17.1.9 [SEQ ID NO: 18] | *Candida boidinii* |

[TABLE 2]

| Target gene | Primer sequence |
| --- | --- |
| fdh [SEQ ID NO: 18] | [SEQ ID NO: 19]: 5'-attgtgagcggata acaatttcacacagga aacagaccatgaagat cgttttagtcttat a-3' [SEQ ID NO: 20]: 5'-gtaccgagctcga attccatttatttctta tcgtgtttac-3' |

TABLE 13

| Target gene | NCBI information | Derived microorganism |
| --- | --- | --- |
| $fdh_{mut}$ | Formate dehydrogenase mutant NCBI_GeneID: 831330 [SEQ ID NO: 21] L229H mutant | *Arabidopsis thaliana* |

[TABLE 14]

| Target gene | Primer sequence |
|---|---|
| fdh$_{mut}$ [SEQ ID NO: 21] | [SEQ ID NO: 22]: 5'-gtaaacacgataag aaataaaggaggaay tcatggcgatgagac aagccgc-3' [SEQ ID NO: 23]: 5'-tcatccgccaaaac agccaagttaccggta ctgaggagcaag-3' |

The DH5α FC5 strain produced by introducing the p100FA2 plasmid into the DH5α AKO1 strain grew from an initial optical density of 0.051 up to an optical density of 0.285 upon culture for 150 hours when only carbon dioxide and formic acid were added to the M9 minimal medium (Table 15). In contrast, the negative control group (DH5α FC1, FC2, FC3) exhibited no strain growth.

TABLE 15

| Ingredient | Content (g/l) |
|---|---|
| Na$_2$HPO$_4$ | 6.8 |
| KH$_2$PO$_4$ | 3 |
| NaCl | 0.5 |
| NH$_4$Cl | 2 |
| MgSO$_4$ | 0.8 |
| NaHCO$_3$ | 4.2 |
| IPTG | 0.24 |
| EDTA | 0.05 |
| Thiamine | 0.002 |
| Trace metal solution | 5 ml |
| Sodium formate | 4.43 |

TABLE 16

| Strain name | Type of gene |
|---|---|
| DH5α AKO | ppsR gene was knocked out and native promoter of ppsA gene was changed to trc promoter in the DH5α_GTPS strain |
| DH5α AKO1 | purT gene was knocked out from the AKO strain |
| DH5α FC1 | DH5α_GTPS harboring p100FA1 |
| DH5α FC2 | AKO harboring p100FA1 |
| DH5α FC3 | AKO1 harboring p100FA1 |
| DH5α FC5 | AKO1 harboring p100FA2 |

Additionally, the number of colony forming units (CFU) was determined in order to measure the increase in the number of cells caused by cell division. The result showed that the initial CFU was 4.8×10$^7$ CFUs/ml (OD$_{600}$ of 0.051), that the CFU increased to 14.1×10$^7$ CFUs/ml (OD$_{600}$ of 0.2) after 50 hours, and that the CFU then gradually decreased to 5.2×10$^7$ CFUs/ml (OD$_{600}$ of 0.285) after 150 hours (FIGS. 3 and 4).

Example 3: Improvement of Growth Rate Through Optimization of Culture Environments and Gene Expression Level The culture conditions of the DH5α FC5 strain produced in Example 2 were optimized, and a plasmid having a attenuated number of copies compared to the above-described plasmid was produced to construct a DH5α FC8 strain that grows rapidly when adding only carbon dioxide and formic acid. In addition, it was observed that the DH5α FC8 strain grew at optical densities from 0.018 up to 3.59 using only carbon dioxide and formic acid when the conventional culture temperature of 37° C. was decreased to 32° C. to increase the cyo expression level and decrease the cyd expression level.

Example 3-1: Optimization of Culture Conditions for Recombinant Strains Capable of Growing Using Only Carbon Dioxide and Formic Acid The culture conditions of the DH5α FC5 strain produced in Example 2 were optimized. In order to reduce the concentration of IPTG, which is an inducer used to promote gene expression, from a conventional concentration of 1 mM to 0.05 mM, the conventional culture conditions (30 ml of culture solution was added to a 100 ml baffle flask) were changed to new culture conditions (50 ml of culture solution was added to a 300 ml baffle flask) to enhance aeration. The result of culture showed that the final cell density increased to 2.16 times that in the case of the conventional culture conditions (FIG. 5).

Example 3-2: Growth Improvement of Recombinant Strains Capable of Growing Using Only Carbon Dioxide and Formic Acid Through Gene Expression Optimization The gene expression level was optimized so as to achieve a sufficiently high cell concentration, because excessive expression of cells beyond the actually required expression level negatively affects cell growth due to the limited nutrient supply upon growth using only carbon dioxide and formic acid. The p15A replication origin having 10 to 12 plasmid copies and the pSC101 replication origin having 1 to 5 plasmid copies were respectively introduced into the p100FA1 plasmid to construct the following plasmids (FIG. 6).

TABLE 17

| Plasmid | Characteristics |
|---|---|
| p184FA | Includes p15A replication origin, chloramphenicol resistance gene, BBa_23100 synthetic promoter, SEQ ID NO: 01 formate-tetrahydrofolate ligase, SEQ ID NO: 02 methenyl tetrahydrofolate cyclohydrolase, SEQ ID NO: 03 methylene-tetrahydrofolate dehydrogenase, SEQ ID NO: 18 formate dehydrogenase, and SEQ ID NO: 21 formate dehydrogenase mutant |
| p518FA | Includes pSC101 replication origin, chloramphenicol resistance gene, BBa_23100 synthetic promoter, SEQ ID NO: 01 formate-tetrahydrofolate ligase, SEQ ID NO: 02 methenyl tetrahydrofolate cyclohydrolase, SEQ ID NO: 03 methylene-tetrahydrofolate dehydrogenase, SEQ ID NO: 18 formate dehydrogenase, and SEQ ID NO: 21 formate dehydrogenase mutant |

PCR was performed using, as templates, the pACYC184 plasmid, containing a chloramphenicol resistance gene, a p15A replication origin, and a BBa_23100 synthetic promoter, and the pJH518 plasmid, containing a chloramphenicol resistance gene, a pSC101 replication origin, and a synthetic promoter BBa_23100, and the primers of SEQ ID NO: 24 to SEQ ID NO: 27, and the amplified gene fragments were collected and purified to produce gene fragments used as plasmid backbones for production of recombinant plasmids.

[SEQ ID NO: 24]:
5'-TGCTGAAAATAAGTCGTCCTGG

ATCCACTAGTTCTAGAGCGG-3'

-continued

[SEQ ID NO: 25]:
5'-ACTATTTACGAAAGTCTCGGGC

TTATCGATACCGTCGACCTCG-3'

[SEQ ID NO: 26]:
5'-TGCTGAAAATAAGTCGTCCTGCA

CCTCGCTAACGGATTCACCAC-3'

[SEQ ID NO: 27]:
5'-ACTATTTACGAAAGTCTCGGGA

ATTACAACTTATATCGTATGGGGC-3'

The plasmid p184FA was introduced into the DH5α AKO1 strain to produce a DH5α FC7 strain, and a plasmid p518FA was introduced into the DH5α FC7 strain to produce a DH5α FC8 strain. When the two strains were cultured under the optimal culture conditions developed in Example 3-1, the DH5α FC8 strain grew from an initial optical density of 0.06 up to 0.607 for 200 hours, which corresponded to 1.14 times that in the case of DH5α FC5, and the DH5α FC8 strain exhibited the highest growth rate (FIG. 7).

TABLE 18

| Strain name | Type of gene |
| --- | --- |
| DH5α FC7 | AKO1 harboring p184FA |
| DH5α FC8 | AKO1 harboring p518FA |

Example 3-3: Improvement of Growth of Recombinant Strains Capable of Growing Using Only Carbon Dioxide and Formic Acid Through Optimization of Expression Levels of Cytochrome bo3 Ubiquinol Oxidase (Cyo) Enzyme and Cytochrome bd-I Ubiquinol Oxidase (Cyd) Enzyme The cytochrome bo3 ubiquinol oxidase (Cyo) enzyme (NCBI GeneID: 945080, 945615, 946897, 944918) and cytochrome bd-I ubiquinol oxidase (Cyd) enzyme (NCBI GeneID: 945341, 945347) are enzymes located in the inner membrane of *E. coli*, and convert reducing power into ATP, which is cellular energy. The related art (Gadgil, M., Kapur, V. & Hu, W S Biotechnol. Prog. 21, 689-699, 2005) reported that, when *E. coli* was cultured at a temperature lower than 37° C., the expression level of Cyo increased and the expression level of Cyd decreased. Among the two enzymes, Cyo converts the reducing power into ATP more efficiently than Cyd. For this reason, the FC8 strain was cultured at 30, 32, and 33° C. in order to increase the expression level of Cyo and decrease the expression level of Cyd. As a result of culture at 32° C., the *E. coli* grew from an initial optical density of 0.018 up to 3.59 for 791.5 hours (FIG. 8), the expression level of Cyo increased, and the expression level of Cyd decreased (FIG. 9). The change in the expression level was determined by comparing the amount of mRNA used for Cyo expression with the amount of mRNA used for Cyd expression through RNA relative quantification using real-time quantification PCR. The primers used in the mRNA relative quantification are shown in Table 19 below.

[TABLE 19]

| Target gene | Primer sequence |
| --- | --- |
| rrsA | [SEQ ID NO: 28]:<br>5'-tgcataaaccgacactggcg-3'<br>[SEQ ID NO: 29]:<br>5'-ttaacctgcttgccgtgctc-3' |
| cyoA | [SEQ ID NO: 30]:<br>5'-tggctgcgttcgaaaaactg-3'<br>[SEQ ID NO: 31]:<br>5'-acatcggcaaacaagtctgg-3' |
| cyoB | [SEQ ID NO: 32]:<br>5'-ttgcgcacttccalaacgtg-3'<br>[SEQ ID NO: 33]:<br>5'-tgaaaccgaacgctttaggc-3' |
| cydA | [SEQ ID NO: 34]:<br>5'-ttacgcactgggcatcattg-3'<br>[SEQ ID NO: 35]:<br>5'-atgcgttcttcatgctgcac-3' |
| cydB | [SEQ ID NO: 36]:<br>5'-aactccattgcaccacactg-3'<br>[SEQ ID NO: 37]:<br>5'-aagaacaaagacgccagcac-3' |

Example 4: Development of Fermentation Process Optimized for Recombinant Strains Capable of Growing Using Only Carbon Dioxide and Formic Acid The growth of the recombinant strains was improved by developing a fermentation process optimized for recombinant strains capable of growing using only carbon dioxide and formic acid. In order to maintain the formic acid concentration and pH of the culture medium at predetermined levels, a 30% formic acid solution was automatically supplied using the pH stat mode to maintain the formic acid concentration (2-3 g/l) and pH (6.8) in the medium at optimal levels during the culture. In addition, in order to improve aeration, the stirring speed was increased by 50 rpm from the initial stirring speed of 500 rpm up to the final stirring speed of 750 rpm whenever the optical density increased by 1. In the optimized fermentation process, the DH5α FC8 strain grew from an initial optical density of 1.02 to an optical density of 7.38 after 450 hours (FIG. 10). In addition, one additional fermentation process was performed. In the optimized fermentation process, the DH5α FC8 strain grew from an initial optical density of 0.91 up to 11.1 after 577 hours (FIG. 11).

Example 5: Development of Recombinant Strain Capable of Growing at Higher Rate by Applying Optimized Fermentation Process to Recombinant Strain Capable of Growing Using Only Carbon Dioxide and Formic Acid In the optimized fermentation process developed in Example 4, the DH5α FC8 strain grew from an initial optical density of 1.02 up to 7.38 after 450 hours, and grew from an initial optical density of 0.91 up to 11.1 after 577 hours (FIGS. 10 and 11). The promoter of the pntAB gene was replaced with the strong trc promoter on the genome of the DH5α FC8 to produce a recombinant *E. coli* strain (DH5α FC9). In the optimized fermentation process developed in Example 4, the DH5α FC9 strain grew from an initial optical density of 1.01 up to 10.2 after 206 hours. This indicates that the DH5α FC9 strain grew at an about 2 times higher rate during the same time (206 hours) when compared with the DH5α FC8 strain, which grew from an initial optical density of 0.91 up to about 5 (FIG. 12).

[TABLE 20]

| Target gene | NCBI information | Derived microorganism |
|---|---|---|
| pntA | H⁺-translocating NAD(P) transhydrogenase subunit alpha NCBI GeneID: 946628 [SEQ ID NO: 40]: 5'-atgcgaattggcataccaagag aacggttaaccaatgaaacccgtgt tgcagcaacgccaaaaacagtggaa cagctgctgaaactgggttttaccg tcgcggtagagagcgggcgggtca actggcaagttttgacgataaagcg tttgtgcaagcgggcgctgaaattg tagaagggaatagcgtctggcagtc agagatcattctgaaggtcaatgcg ccgttagatgatgaaattgcgttac tgaatcctgggacaacgctggtgag ttttatctggcctgcgcagaatccg gaattaatgcaaaaactgcggaac gtaacgtgaccgtgatggcgatgga ctctgtgccgcgtatctcacgcgca caatcgctggacgcactaagctcga tggcgaactcgccggttatcgcgc cattgttgaagcggcacatgaattt gggcgcttctttaccgggcaaatta ctgccggccgggaaagtgccaccgc aaaagtgatggtgattggtgcgggt gttgcaggtctggccgccattggcg cagcaaacagtctcggcgcgattgt gcgtgcattcgacacccgcccggaa gtgaaagaacaagttcaaagtatgg gcgcggaattcctcgagctggattt taaagaggaagctggcagcggcgat ggctatgccaaagtgatgtcggacg cgttcatcaaagcggaaatggaact ctttgccgcccaggcaaaagaggtc gatatcattgtcaccaccgcgctta ttccaggcaaaccagcgccgaagct aattacccgtgaaatggttgactcc atgaaggcgggcagtgtgattgtcg acctggcagcccaaaacggcggcaa ctgtgaatacaccgtgccgggtgaa atcttcactacggaaaatggtgtca aagtgattggttataccgatcttcc gggccgtctgccgacgcaatcctca cagctttacggcacaaacctcgtta atctgctgaaactgttgtgcaaaga gaaagacggcaatatcactgttgau tigatgatgtggtgattcgcggcgt gaccgtgatccgtgcgggcgaaatt acctggccggcaccgccgaticagg tatcagctcagccgcaggcggcaca aaaagcggcaccggaagtgaaaact gaggaaaatgtacctgctcaccgt ggcgtaaatacgcgttgatggcgct ggcaatcattctttttggctggatg gcaagcgttgcgccgaaagaattcc ttgggcacttcaccgttttcgcgct ggcctgcgttgtcggttattacgtg gtgtggaatgtatcgcacgcgctgc atacaccgttgatgtcggtccaccaa cgcgatttcagggattattgttgtc ggagcactgttgcagattggccagg gcggctgggttagcttccttagttt tatcgcggtgcttatagccagcatt aatattttcggtggcttcaccgtga ctcagcgcatgctgtgaaaatgttccg caaaaattaa-3' | Escherichia coli |
| pntB | H⁺-translocating NAD(P) transhydrogenase subunit beta NCBI GeneID: 946144 [SEQ ID NO: 41]: 5'-atgtctggaggattagttacagctg | Escherichia coli |

[TABLE 20]-continued

| Target gene | NCBI information | Derived microorganism |
|---|---|---|
| | catacattgttgccgcgatcctgtt tatcttcagtctggccggtctttcg aaacatgaaacgtctcgccagggta acaacttcggtatcgccgggatggc gattgcgttaatcgcaaccattttt ggaccggatacgggtaatgttggct ggatcttgctggcgatggtcattgg tggggcaattggtatccgtctggcg aagaaagttgaaatgaccgaaatgc cagaactggtggcgatcctgcatag cttcgtgggtctggccggcagtgctg gttggctttaacagctatctgcatc atgaegegggaatggeacegattet ggteaatattcacctgacggaagtg ttcctcggtatcttcatcggggcgg taacgttcacgggttcggtggtggc gttcggcaaactgtgtggcaagatt tcgtctaaaccattgatgctgccaa accgtcacaaaatgaacctggcgge tctggtcgtttccttcctgctgctg attgtatttgttcgcacggacagcg tcggcctgcaagtgctggcattgct gataatgacegcaattgcgctggta ttcggctggcatttagtcgcctcca tcggtggtgcagatatgccagtggt ggtgtcgatgctgaactcgtactcc ggctgggcggctgcggctgcgggct ttatgctcagcaacgacctgctgat tgtgaccggtgcgctggtcggttct tcgggggctatcctttcttacatta tgtgtaaggcgatgaaccgttcctt tatcagcgttattgcgggtggttc ggcaccgacggctcttctactggcg atgatcaggaagtgggtgagcaccg cgaaatcaccgcagaagagacagcg gaactgctgaaaaactcccattcag tgatcattactccggggtacggcat ggcagtcgcgcaggcgcaatatcct gtcgctgaaattactgagaaattgc gcgctcgtggtattaatgtgcgttt cggtatccaccggtcgcggggcgt ttgcctggacatatgaacgtattgc tggctgaagcaaaagtaccgtatga catcgtgctggaaatggacgagatc aatgatgactttgctgataccgata ccgtactggtgattggtgctaacga tacggttaacccggcggcgcaggat gatccgaagagtccgattgctggta tgcctgtgctggaagtgtggaaagc gcagaacgtgattgtctttaaacgt tcgatgaacactggctatgctggtg tgcaaaacccgctgttcttcaagga aaacacccacatgctgtttggtgac gccaaagccagcgtggatgcaatcc tgaaagctctgtaa-3' | |

Example 6: Introduction of Formic Acid Assimilation Metabolic Pathway Into Microorganisms of Genus *Mannheimia* and Verification of Formic Acid Assimilation Ability It was found that formic acid assimilation proceeds even in host microorganisms having a central carbon metabolic pathway as well as *E. coli* through the formic acid assimilation metabolic pathway developed in the present invention. In this example, the formic acid assimilation metabolic pathway was introduced into the microorganism of the genus *Mannheimia*, and whether or not formic acid assimilation was performed was identified through carbon isotope analysis.

First, a plasmid containing the genes ftl, fch, and mtd, involved in the formic acid assimilation pathway, was introduced into a microorganism of the genus *Mannheimia* to produce a recombinant microorganism including the formic acid assimilation pathway. Specifically, the foreign gene fragments required for plasmid production were prepared through PCR using the p100THF plasmid prepared in Example 1, having the corresponding gene as a template, and using primers designed for amplifying the corresponding gene, followed by collecting and purifying the amplified gene fragments. The primer sequences are shown in Table 21 below.

[TABLE 21]

| Target gene | Primer sequence |
|---|---|
| ftfL-fch-mtd | [SEQ ID NO: 38]:<br>5'-ttatcaactctactgggg aggaattcatgccctcagata tcgagatc-3'<br>[SEQ ID NO: 39]:<br>5'-tctagaggatccccgggt acctcaggccatttccttggc c-3' |

A plasmid containing genes encoding the above enzymes was produced to construct the formic acid assimilation pathway.

TABLE 22

| plasmid | Characteristics |
|---|---|
| pMS3-THF | Includes pMB1 replication origin, *Mannheimia* replication origin, ampicillin resistance gene, frdA promoter, SEQ ID NO: 01 formate-tetrahydrofolate ligase, SEQ ID NO: 02 methenyl tetrahydrofolate cyclohydrolase, and SEQ ID NO: 03 methylene-tetrahydrofolate dehydrogenase |

Plasmids were produced from the plasmid backbone gene fragments and amplified gene fragments using the Gibson assembly method (Gibson et al., *Nat. Methods*, 6:5, 343-345, 2009), which is commonly used for the assembly of gene fragments, and each plasmid was produced so as to include one or more of the foreign genes set forth in Table above.

The recombinant plasmid produced by the method described above was transformed into *Mannheimia* to produce recombinant *Mannheimia*. The *Mannheimia* used in the present invention was *Mannheimia succiniciproducens* LPK7, and transformation into *Mannheimia* was carried out using electroporation commonly used in the art.

For formic acid assimilation ability analysis, the recombinant *Mannheimia* strain (LPK7_FTF) introduced with the formic acid assimilation metabolic pathway and the negative control strain (LPK7) introduced with the empty vector were cultured in brain heart infusion (BHI) medium supplemented with 2 g/l of glycine and 4.43 g/l of $^{13}$C-labeled formate, and then the ratio of carbon isotopes contained in serine contained in biomass was measured. When formic acid assimilation is performed by the formic acid assimilation pathway, the formic-acid-derived carbon is located at carbon 1 of serine by the formic acid assimilation metabolic pathway shown in FIG. 1. The result of the measurement showed that $^{13}$C carbon derived from formic acid was detected in about 19.5% of the total serine contained in the biomass in the LPK7_FTF strain introduced with the formic acid assimilation metabolic pathway, but $^{13}$C carbon was not detected in serine at all in the negative control strain (FIG. 13).

[TABLE 23]

Gene sequences used in this example

| Gene name | Gene sequence (5-3) |
|---|---|
| ftfL<br>[SEQ ID NO: 1] | atgccctcagatatcgagatcgccc<br>gcgcggcgaccctgaagccgatcgc<br>ccaggtcgccgaaaagctcggcatc<br>ccggacgaggcgcttcacaattacg<br>gcaagcacatcgccaagatcgacca<br>cgacttcatcgcctcgctcgagggt<br>aagcccgagggcaagctggtgctcg<br>tcaccgcgatctcgccgacgcctgc<br>gggcgagggcaagaccaccacgact<br>gtggggctcggcgacgcgctcaacc<br>gcatcggcaagcgggcggtgatgtg<br>cctgcgcgagccctcgctcggcccc<br>tgcttcggcatgaagggcggcgcgg<br>ccggtggcggcaaggcgcaggtcgt<br>gccgatggagcagatcaacctgcac<br>ttcaccggcgacttccacgccatca<br>cctcggcgcactcgctcgccgccgc<br>tctgatcgacaaccacatctactgg<br>gccaacgagctcaacatcgacgtgc<br>gccgcatccactggcgccgcgtggt<br>cgacatgaacgaccgagcgctgcgc<br>gcgatcaaccagtcgctcggcggcg<br>tcgccaacggctttccgcgtgagga<br>cggcttcgacatcaccgtcgcctcc<br>gaggtgatggcggtgttctgcctcg<br>ccaagaatctggctgacctcgaaga<br>gcggctcggccgcatcgtcatcgcc<br>gagacccgcgaccgcaagccggtga<br>cgctggccgacgtgaaggcgaccgg<br>tgcgatgaccgttctcctcaaggac<br>gcgcttcagccgaacctcgtgcaga<br>cgctggagggcaacccggccctgat<br>ccatggcggcccgttcgccaacatc<br>gcccacggctgcaactcggtgatcg<br>ccacccgcaccggcctgcggctggc<br>cgactacaccgtcaccgaggccggc<br>ttcggcgcggatctcggcgcggaga<br>agttcatcgacatcaagtgccgcca<br>gaccggcctcaagccctcgtcggtg<br>gtgatcgtcgccacgatccgcgccc<br>tcaagatgcatggcggcgtcaacaa<br>gaaggatctccaggctgagaacctc<br>gacgcgctggagaagggcttcgcca<br>acctcgagcgccacgtgaataacgt<br>ccggagcttcggcctgccggtggtg<br>gtgggtgtgaaccacttcttccagg<br>acaccgacgccgagcatgcccggtt<br>gaaggagctgtgccgcgaccggctc<br>caggtcgaggcgatcacctgcaagc<br>actgggcggagggcggcgcgggcgc<br>cgaggcgctggcgcaggccggtggtg<br>aagctcgccgagggcgagcagaagc<br>cgctgaccttcgcctacgagaccga<br>gacgaagatcaccgacaagatcaag<br>gcgatcgcgaccaagctctacggcg<br>cggccgacatccagatcgagtcgaa<br>ggccgccaccaagctcgccggcttc<br>gagaaagacggctacggcaaattgc<br>cggtctgcatggccaagacgcagta<br>ctcgttctcgaccgacccgaccctg<br>atgggcgcgccctcgggccacctcg<br>tctcggtgcgcgacgtgcgcctctc<br>ggcgggcgccggcttcgtcgtggtg<br>atctgcggtgagatcatgaccatgc<br>cgggtctgccaaaagtgccggcggc<br>ggacaccatccgcctggacgccaac<br>ggtcagatcgacgggctgttctag |
| fch<br>[SEQ ID NO: 2] | atggccggcaacgagacgatcgaaa<br>cattcctcgacggcctggcgagctc<br>ggccccgaccccggcggcggcggt<br>gccgccgcgatctccggcgccatgg<br>gcgcggcgctggtgtcgatggtgtg<br>caacctcaccatcggcaagaagaag<br>tatgtcgaggtcgaggccgacctga<br>agcaggtgctggagaagtcggaagg |

[TABLE 23]-continued

Gene sequences used in this example

| Gene name | Gene sequence (5-3) |
|---|---|
| | cctgcgccgcacgctcaccggcatg<br>atcgccgacgacgtcgaggctttcg<br>acgcggtgatgggcgcctacgggct<br>gccgaagaacaccgacgaagagaag<br>gccgcccgcgccgccaagattcaag<br>aggcgctcaaaaccgcgaccgacgt<br>gccgctcgcctgctgccgcgtctgc<br>cgcgaggtgatcgacctggccgaga<br>tcgtcgccgagaagggcaatctcaa<br>cgtcatctcggatgccgcgtcgcc<br>gtgctctcggcctatgccggcctgc<br>gctcggcggcccttaacgtctacgt<br>caacgccaagggcctcgacgaccgc<br>gccttcgccgaggagcggctgaagg<br>agctggagggcctactgccgaggc<br>gggcgcgctcaacgagcggatctac<br>gagaccgtgaagtccaaggtaaact<br>ga |
| mtdA<br>[SEQ ID NO: 3] | atgtccaagaagctgctcttccagt<br>tcgcaccgatgccacgccgagcgt<br>cttcgacgtcgtcgtcggctacgac<br>ggcggtgccgaccacatcaccggct<br>acggcaacgtcacgcccgacaacgt<br>cggccgctatgtcgacggcacgatc<br>tacacccgcggcggcaaggagaagc<br>agtcgacggcgatcttcgtcggcgg<br>cggcgacatggcggccggcgagcgg<br>gtgttcgaggcggtgaagaagcgct<br>tcttcggcccgttccgcgtgtcctg<br>catgctggattcgaacggctccaac<br>acgaccgctgcgcgggcgtggcgc<br>tcgtcgtcaaggcggcggcggctc<br>ggtcaagggcaagaaggccgtcgtg<br>ctcgcggggcaccggcccggtcggca<br>tgcgctcggcggcgctgcttgccgg<br>cgagggcgccgaggtcgtgctgtgc<br>gggcgcaagctcgacaaggcgcagg<br>ccgcggccgattccgtgaacaagcg<br>cttcaaggtaacgtcaccgcggcc<br>gagaccgcggacgacgcttcgcgtg<br>ccgaggcgtgaagggcgcccatt<br>cgtcttcaccgccggtgcgatcggc<br>cttgaactgctgccgcaggcagcct<br>ggcagaacgagagttcgatcgagat<br>cgtggccgactacaacgcccagccg<br>ccgctcggcatcggcgggatcgatg<br>cgaccgacaaaggcaaggaatacgg<br>cggaaagcgcgccttcggtgcgctc<br>ggcatcggcggcttgaagctcaagc<br>tgcaccgcgcctgcatcgccaagct<br>gttcgagtcgagcgaaggcgtcttc<br>gacgccgaggagatctacaagctgg<br>ccaaggaaatggcctga |
| gcvT<br>[SEQ ID NO: 10] | atggcacaacagactcctttgtacg<br>aacaacacgctttgcggcgctcg<br>catggtggatttccacggctggatg<br>atgccgctgcattacggttcgcaaa<br>tcgacgaacatcatgcggtacgtac<br>cgatgccggaatgtttgatgtgtca<br>catatgaccatcgtcgatcttcgcg<br>gcagccgcaccggagtttctgcg<br>ttatctgctggcgaacgatgtggcg<br>aagctcaccaaaagcggcaaagccc<br>tttactcggggatgttgaatgcctc<br>tggcggtgtgatagatgacctcatc<br>gtctactactttactgaagatttct<br>tccgcctcgttgttaactccgccac<br>ccgcgaaaagacctctcctggatt<br>acccaacacgctgaacctttcggca<br>tcgaaattaccgttcgtgatgacct<br>ttccatgattgccgtgcaagggcg<br>aatgcgcaggcaaaagctgccacac<br>tgtttaatgacgcccagcgtcaggc<br>ggtggaagggatgaaaccgttctt |

| Gene name | Gene sequence (5-3) |
|---|---|
| | ggcgtgcaggcgggcgatctgttta<br>ttgccaccactggttataccggtga<br>agcgggctatgaaattgcgctgccc<br>aatgaaaaagcggccgatttctggc<br>gtgcgctggtggaagcgggtgttaa<br>gccatgtggcttgggcgcgcgtgac<br>acgctgcgtctggaagcgggcatga<br>atctttatggtcaggagatggacga<br>aaccatctctcctttagccgccaac<br>atgggctggaccatcgcctgggaac<br>cggcagatcgtgactttatcggtcg<br>tgaagccctggaagtgcagcgtgag<br>catggtacagaaaaactggttggtc<br>tggtgatgaccgaaaaaggcgtgct<br>gcgtaatgaactgccggtacgcttt<br>accgatgcgcagggcaaccagcatg<br>aaggcattatcaccagcgggtacttt<br>ctccccgacgctgggttacagcatt<br>gcgctggcgcgcgtgccggaaggta<br>ttggcgaaacggcgattgtgcaaat<br>tcgcaaccgtgaaatgccggttaaa<br>gtgacaaaacctgttttgtgcta<br>acggcaaagccgtcgcgtga |
| gcvH<br>[SEQ ID NO: 11] | atgagcaacgtaccagcagaactga<br>aatacagcaaagaacacgaatggct<br>gcgtaaagaagccgacggcacttac<br>accgttggtattaccgaacatgctc<br>aggagctgttaggcgatatggtgtt<br>tgttgacctgccggaagtgggcgca<br>acggttagcgcgggcgatgactgcg<br>cggttgccgaatcgtaaaagcggc<br>gtcagacatttatgcgccagtaagc<br>ggtgaaatcgtggcggtaaacacg<br>cactgagcgattccccggaactggt<br>gaacagcgaaccgtatgcaggcggc<br>tggatctttaaaatcaaagccagcg<br>atgaaagcgaactgaatcactgct<br>ggatgcgaccgcatacgaagcattg<br>ttagaagacgagtaa |
| gcvP<br>[SEQ ID NO: 12] | atgacacagacgttaagccagcttg<br>aaaacagcggcgcttttattgaacg<br>ccatatcggaccggacgccgcgcaa<br>cagcaagaaatgctgaatgccgttg<br>gtgcacaatcgttaaacgcgctgac<br>cggccagattgtgccgaaagatatt<br>caacttgcgacaccaccgcaggttg<br>gcgcaccggcgaccgaatacgccgc<br>actggcagaactcaaggctattgcc<br>agtcgcaataaacgcttcacgtctt<br>acatcggcatgggttacaccgccgt<br>gcagctaccgccggttatcctgcgt<br>aacatgctgaaaatccgggctggt<br>ataccgcgtacactccgtatccaacc<br>tgaagtctcccaggggccgccttgaa<br>gcactgctcaacttccagcaggtaa<br>cgctggattgactggactggatat<br>ggcctctgcttctcttctggacgag<br>gccaccgctgccgccgaagcaatgg<br>cgatggcgaaacgcgtcagcaaact<br>gaaaaatgccaaccgcttcttcgtg<br>gcttccgatgtgcatccgcaaacgc<br>tggatgtggtccgtactcgtgccga<br>aacctttggttttgaagtgattgtc<br>gatgacgcgcaaaagtgctcgacc<br>atcaggacgtcttcggcgtgctgtt<br>acagcaggtaggcactaccggtgaa<br>attcacgactacactgcgcttatta<br>gcgaactgaaatcacgcaaaattgt<br>ggtcagcgttgccgccgatattatg<br>gcgctggtgctgttaactgcgccgt<br>gtaaacagggcgcggatattgttt<br>tggttcggcgcaacgcttcggcgta<br>ccgatgggctacggtggcccacacg<br>cggcattctttgcggcgaaagatga |

[TABLE 23]-continued

Gene sequences used in this example

| Gene name | Gene sequence (5-3) |
| --- | --- |
| | atacaaacgctcaatgccgggccgt |
| | attatcggtgtatcgaaagatgcag |
| | ctggcaataccgcgctgcgcatggc |
| | gatgcagactcgcgagcaacatatc |
| | cgccgtgagaaagcgaactccaaca |
| | tttgtacttccaggtactgctggc |
| | aaacatcgccagcctgtatgccgtt |
| | tatcacggcccggttggcctgaaac |
| | gtatcgctaaccgcattcaccgtct |
| | gaccgatatcctggcggcgggcctg |
| | caacaaaaaggtctgaaactgcgcc |
| | atgcgcactatttcgacaccttgtg |
| | tgtggaagtggccgacaaagcgggc |
| | gtactgacgcgtgccgaagcggctg |
| | aaatcaacctgcgtagcgatattct |
| | gaacgcggttgggatcacccttgat |
| | gaaacaaccacgcgtgaaaacgtaa |
| | tgcagcttttcaacgtgctgctggg |
| | cgataaccacggcctggacatcgac |
| | acgctggacaaagacgtggctcacg |
| | acagccgctctatccagcctgcgat |
| | gctcgcgacacgaaatcctcacc |
| | catccggtgtttaatcgctaccaca |
| | gcgaaaccgaaatgatgcgctatat |
| | gcactcgctggagcgtaaagatctg |
| | gcgctgaatcaggcgatgatcccgc |
| | tgggttcctgcaccatgaaactgaa |
| | cgccgccgccgagatgatcccaatc |
| | acctggccggaatttgccgaactgc |
| | acccgttctgcccgccggagcaggc |
| | cgaaggttatcagcagatgattgcg |
| | cagctggctgactggctggtgaaac |
| | tgaccggttacgacgccgtttgtat |
| | gcagccgaactctggcgcacagggc |
| | gaatacgcgggcctgctggcgattc |
| | gtcattatcatgaaagccgcaacga |
| | agggcatcgcgatatctgcctgatc |
| | ccggcttctgcgcacggaactaacc |
| | ccgcttctgcacatatggcaggaat |
| | gcaggtggtggttgtggcgtgtgat |
| | aaaaacggcaacatcgatctgactg |
| | atctgcgcgcgaaagcggaacaggc |
| | gggcgataacctctcctgtatcatg |
| | gtgactttatccttctacccacggcg |
| | tgtatgaaaaacgatccgtgaagt |
| | gtgtgaagtcgtgcatcagttcggc |
| | ggtcaggtttaccttgatggcgcga |
| | acatgaacgccaggttggcatcac |
| | ctcgccgggctttattggtgcggac |
| | gtttcacacccttaacctactataaa |
| | cttttctgcattccgcacggcggtgg |
| | tggtccgggtatgggaccgatcggc |
| | gtgaaagcgcatttggcaccgtttg |
| | taccgggtcatagcgtggtgcaaat |
| | cgaaggcatgttaacccgtcagggc |
| | gcggtttctgcggcaccgttcggta |
| | gcgcctctatcctgccaatcagctg |
| | gatgtacatccgcatgatgggcgca |
| | gaagggctgaaaaaagcaagccagg |
| | tggcaatcctcaacgccaactatat |
| | tgccagccgcctgcaggatgccttc |
| | ccggtgctgtataccggtcgcgacg |
| | gtcgcgtggcgcacgaatgtattct |
| | cgatattcgcccgctgaaagaagaa |
| | accggcatcagcgagctggatattg |
| | ccaagcgcctgatcgactacggttt |
| | ccacgcgccgacgatgtcgttcccg |
| | gtggcgggtacgctgatggttgaac |
| | cgactgaatctgaaagcaaagtgga |
| | actggatcgctttatcgacgcgatg |
| | ctgctatccgcgcagaaattgacc |
| | aggtgaaagccggtgtctggcgct |
| | ggaagataacccgctggtgaacgcg |
| | ccgcacattcagagcgaactggtcg |
| | ccgagtgggcgcatccgtacagccg |
| | tgaagttgcggtattcccggcaggt |
| | gtggcagacaaatactggccgacag |
| | tgaaacgtctggatgatgtttacgg |
| | cgaccgtaacctgttctgctcctgc |
| | gtaccgattagcgaataccagtaa |
| pflB [SEQ ID NO: 13] | atgtccgagcttaatgaaaagttag |
| | ccacagcctgggaaggttttaccaa |
| | aggtgactggcagaatgaagtaaac |
| | gtccgtgacttcattcagaaaaact |
| | acactccgtacgagggtgacgagtc |
| | cttcctggctggcgctactgaagcg |
| | accaccaccctgtgggacaaagtaa |
| | tggaaggcgttaaactggaaaaccg |
| | cactcacgcgccagttgactttgac |
| | accgctgttgcttccaccatcacct |
| | ctcacgacgctggctacatcaacaa |
| | gcagcttgagaaaatcgttggtctg |
| | cagactgaagctccgctgaaacgtg |
| | ctcttatcccgttcggtggtatcaa |
| | aatgatcgaaggttcctgcaaagcg |
| | tacaaccgcgaactggatccgatga |
| | tcaaaaaaatcttcactgaataccg |
| | taaaactcacaacaggcgtgttc |
| | gacgtttacactccggacatcctgc |
| | gttccgtaaatctggtgttctgac |
| | cggtctgccagatgcatatggccgt |
| | ggccgtatcatcggtgactaccgtc |
| | gcgttgcgctgtacggtatcgacta |
| | cctgatgaaagacaaactggcacag |
| | ttcacttctctgcaggctgatcctg |
| | aaaacggcgtaaacctggaacagac |
| | tatccgtctgcgcgaagaaatcgct |
| | gaacagcaccgcgctctgggtcaga |
| | tgaaagaaatggctgcgaaatacg |
| | ctacgacatctctggtccggctacc |
| | aacgctcaggaagctatccagtgga |
| | cttacttcggctacctggctgctgt |
| | taagtctcagaacgGtgctgcaatg |
| | tccttcggtcgtacctccacccttcc |
| | tggatgtgtacatcgaacgtgacct |
| | gaaagctggcaagatcaccgaacaa |
| | gaagcgcaggaaatggttgaccacc |
| | tggtcatgaaactgcgtatggttcg |
| | cttcctgcgtactccggaatacgat |
| | gaactgttctctggcgacccgatct |
| | gggcaaccgaatctatcggtggtat |
| | gggcctcgacggtcgtaccctggtt |
| | accaaaaacagcttccgttcctga |
| | acaccctgtacaccatgggtccgtc |
| | tccggaaccgaacatgaccattctg |
| | tggtctgaaaaactgccgctgaact |
| | tcaagaaattcgccgctaaagtgtc |
| | catcgacacctcttctctgcagtat |
| | gagaacgatgacctgatgcgtccgg |
| | acttcaacaacgatgactacgctat |
| | tgcttgctgcgtaagcccgatgatc |
| | gttggtaaacaaatgcagttcttcg |
| | gtgcgcgtgcaaacctggcgaaaac |
| | catgctgtacgcaatcaacggcggc |
| | gttgacgaaaaactgaaaatgcagg |
| | ttggtccgaagtctgaaccgatcaa |
| | aggcgatgtcctgaactatgatgaa |
| | gtgatggacgcatggatcacttca |
| | tggactggctggctaaacagtacat |
| | cactgcactgaacatcatccactac |
| | atgcacgacaagtacagctacgaag |
| | cctctctgatggcgctgcacgaccg |
| | tgacgttatccgcaccatggcgtgt |
| | ggtatcgctggtctgtccgttgctg |
| | ctgactccctgtctgcaatcaaata |
| | tgcgaaagttaaaccgattcgtgac |
| | gaagacggtctggctatcgacttcg |
| | aaatcgaaggcgaataccogcagtt |
| | tggtaacaatgatccgcgtgtagat |
| | gacctggctgttgacctggtagaac |
| | gttttcatgaagaaattcagaaact |

[TABLE 23]-continued

Gene sequences used in this example

| Gene name | Gene sequence (5-3) |
| --- | --- |
| | gcacacctaccgtgacgctatcccg |
| | actcagtctgttctgaccatcactt |
| | ctaacgttgtgtatggtaagaaaac |
| | gggtaacaccccagacggtcgtcgt |
| | gctggcgcgccgttcggacccgggtg |
| | ctaacccgatgcacggtcgtgacca |
| | gaaaggtgcagtagcctctctgact |
| | tccgttgctaaactgccgtttgctt |
| | acgctaaagatggtatctcctacac |
| | cttctctatcgttccgaacgcactg |
| | ggtaaagacgacgaagttcgtaaga |
| | ccaacctggctggtctgatggatgg |
| | ttacttccaccacgaagcatccatc |
| | gaaggtggtcagcacctgaacgtta |
| | acgtgatgaaccgtgaaatgctgct |
| | cgacgcgatggaaaacccggaaaaa |
| | tatccgcagctgaccatccgtgtat |
| | ctggctacgcagtacgtttcaactc |
| | gctgactaaagaacagcagcaggac |
| | gttattactcgtaccttcactcaat |
| | ctatgtaa |
| serA [SEQ ID NO: 14] | atggcaaaggtatcgctggagaaag |
| | acaagattaagtttctgctggtaga |
| | aggcgtgcaccaaaaggcgctgaa |
| | agccttcgtgcagctggttacacca |
| | acatcgaatttcacaaaggcgcgct |
| | ggatgatgaacaattaaaagaatcc |
| | atccgcgatgcccacttcatcggcc |
| | tgcgatcccgtaccatctgactga |
| | agacgtgatcaacgccgcagaaaaa |
| | ctggtcgctattggctgtttctgta |
| | tcggaacaaaccaggttgatctgga |
| | tgccgcggcaaagcgcggagatcccg |
| | gtatttaacgcaccgttctcaaata |
| | cgcgctctgttgcggagctggtgat |
| | tggcgaactgctgctgctattgcgc |
| | ggcgtgccggaagccaatgctaaag |
| | cgcaccgtggcgtgtggaacaaact |
| | ggcggcggttctttgaagcgcgc |
| | ggcaaaaagctgggtatcatcggct |
| | acggtcatattggtacgcaattggg |
| | cattctggctgaatcgctgggaatg |
| | tatgttactttttatgatattgaaa |
| | ataaactgccgctgggcaacgccac |
| | tcaggtacagcatcttttctgacctg |
| | ctgaatatgagcgatgtggtgagtc |
| | tgcatgtaccagagaatccgtccac |
| | caaaaatatgatgggcgcgaaagaa |
| | attcactaatgaagcccggctgc |
| | tgctgattaatgcttcgcgcgtac |
| | tgtggtggatattccggcgctgtgt |
| | gatgcgctggcgagcaaacatctgg |
| | cgggggcggcaatcgacgtattccc |
| | gacggaaccggcgaccaatagcgat |
| | ccatttacctctccgctgtgtgaat |
| | tcgacaacgtccttctgacgccaca |
| | cattggcggttcgactcaggaagcg |
| | caggagaatatcggcctggaagttg |
| | cgggtaaattgatcaagtattctga |
| | caatggctcaacgctctctgcggtg |
| | aacttcccggaagtctcgctgccac |
| | tgcacggtgggcgtcgtctgatgca |
| | catccacgaaaaccgtccgggcgtg |
| | ctaactgcgctgaacaaaatctcg |
| | ccgagcagggcgtcaacatcgccgc |
| | gcaatatctgcaaacttccgcccag |
| | atgggttatgtggttattgatattg |
| | aagccgacgaagacgttgccgaaaa |
| | agcgctgcaggcaatgaaagctatt |
| | ccgggtacccattcgcgccgtctgc |
| | tgtactaa |
| gcvR [SEQ ID NO: 15] | ttgacactgtcatcgcaacattatc |
| | tggtgatcactgcgttgggtgccga |
| | tcgccctggaattgtgaacaccatc |
| ppsR [SEQ ID NO: 16] | acccgtcatgtcagtagttgcggct |
| | gtaatattgaagacagtcgcctggc |
| | gatgctgggagaagagttcacgttt |
| | attatgctgctttccggttcatgga |
| | atgccattactctgattgaatcaac |
| | gttaccgttgaaaggtgccgaactg |
| | gatcttttaatcgtgatgaagcgca |
| | cgacggcgcgtccgcgtccgccaat |
| | gccagcatctgtctgggttcaggtc |
| | gatgtggcagactcccccgcatttaa |
| | ttgaacgcttcacagcacttttcga |
| | cgcgcatcatatgaacattgcggag |
| | ctggtgtcgcgcacgcaacctgctg |
| | aaaatgaacgggctgcgcagttgca |
| | tattcagataaccgcccacagcccc |
| | gcatctgcgggacgcagcaaatattg |
| | agcaagcgttcaaagccctatgtac |
| | agaactcaatgcacaaggcagtatt |
| | aacgtcgtcaattattcccaacatg |
| | atgaacaggatggagttaagtaa |
| purT [SEQ ID NO: 17] | atgacgttattaggcactgcgctgc |
| | gtccggcagcaactcgcgtgatgtt |
| | attaggctccggtgaactgggtaaa |
| | gaagtggcaatcgagtgtcagcgtc |
| | tcggcgtagaggtgattgccgtcga |
| | tcgctatgccgacgcaccagccatg |
| | catgtcgccgatcgctcccatgtca |
| | ttaatatgcttgatggtgatgcatt |
| | acgccgtgtggttgaactgaaaaa |
| | ccacattatatcgtgccggagatcg |
| | aagctattgccaccgatatgctgat |
| | ccaacttgaagaggaaggactgaat |
| | gttgtcccctgcgctcgcgcaacga |
| | aattaacgatgaatcgcgagggtat |
| | ccgtcgctggcggcagaagagctg |
| | cagctgcccacttccacttatcgtt |
| | ttgccgatagcgaaagccttttccg |
| | cgaggcggttgctgacattggctat |
| | ccctgcattgtaaaaccggtgatga |
| | gctcttccggcaaggggcagacgtt |

[TABLE 23]-continued

Gene sequences used in this example

| Gene name | Gene sequence (5-3) |
|---|---|
|  | tattcgttctgcagagcaacttgct |
|  | caggcatggaagtacgctcagcaag |
|  | gcggtcgcgccggagcgggccgcgt |
|  | aattgttgaaggcgtcgttaagttt |
|  | gacttcgaaattaccctgctaaccg |
|  | tcagcgcggtggatggcgtccattt |
|  | ctgtgcaccagtaggtcatcgccag |
|  | gaagatggcgactaccgtgaatcct |
|  | ggcaaccacagcaaatgagcccgct |
|  | tgcccttgaacgtgcgcaggagatt |
|  | gcccgtaaagtggtgctggcactgg |
|  | gcggttatgggttgtttggtgtcga |
|  | gctatttgtctgtggtgatgaggtg |
|  | attttcagtgaggtctcccctcgtc |
|  | cacatgataccgggatggtgacgtt |
|  | aatttctcaagatctctcagagttt |
|  | gccctgcatgtacgtgccttcctcg |
|  | gacttccggttggcgggatccgtca |
|  | gtatggtcctgcagcttctgccgtt |
|  | attctgccacaactgaccagtcaga |
|  | atgtcacgtttgataatgtgcagaa |
|  | tgccgtaggcgcagatttgcagatt |
|  | cgtttatttggtaagccggaaattg |
|  | atggcagccgtcgtctgggggtggc |
|  | actggctactgcagagagtgttgtt |
|  | gacgccattgaacgcgcgaagcacg |
|  | ccgccggacaggtaaaagtacaggg |
|  | ttaa |
| fdh [SEQ ID NO: 18] | atgaagatcgttttagtcttatatg |
|  | atgctggtaagcacgctgctgatga |
|  | agaaaaattatatggttgtactgaa |
|  | aataaattaggtattgctaattggt |
|  | taaaagatcaaggtcatgaactaat |
|  | tactacttctgataaagaaggtgaa |
|  | acaagtgaattggataaacatatcc |
|  | cagatgctgatattatcatcaccac |
|  | tcctttccatcctgcttatatcact |
|  | aaggaaagacttgacaaggctaaga |
|  | acttaaaattagtcgttgtcgctgg |
|  | tgttggttctgatcacattgattta |
|  | gattatattaatcaaacaggtaaga |
|  | aaatctcagtcttggaagttacagg |
|  | ttctaatgttgtctctgttgctgaa |
|  | cacgttgtcatgaccatgcttgtct |
|  | tggttagaaatttcgttccagcaca |
|  | tgaacaaattattaaccacgattgg |
|  | gaggttgctgctatcgctaaggatg |
|  | cttacgatatcgaaggtaaaactat |
|  | tgctaccattggtgctggtagaatt |
|  | ggttacagagtcttggaaagattac |
|  | tccctttaatccaaaagaattatt |

[TABLE 23]-continued

Gene sequences used in this example

| Gene name | Gene sequence (5-3) |
|---|---|
|  | atactacgattatcaagctttacca |
|  | aaagaagctgaagaaaaagttggtg |
|  | ctagaagagttgaaaatattgaaga |
|  | attagttgctcaagctgatatcgtt |
|  | acagttaatgctccattacacgcag |
|  | gtacaaaaggtttaattaataagga |
|  | attattatctaaatttaaaaaaggt |
|  | gcttggttagtcaataccgcaagag |
|  | gtgctatttgtgttgctgaagatgt |
|  | tgcagcagctttagaatctggtcaa |
|  | ttaagaggttacggtggtgatgttt |
|  | ggttcccacaaccagctccaaagga |
|  | tcacccatggagagatatgagaaat |
|  | aaatatggtgctggtaatgccatga |
|  | ctcctcactactctggtactactt |
|  | agatgctcaaacaagatacgctgaa |
|  | ggtactaaaaatatcttggaatcat |
|  | tctttactggtaaatttgattacag |
|  | accacaagatattatcttattaaat |
|  | ggtgaatacgttactaaagcttacg |
|  | gtaaacacgataagaaataa |

INDUSTRIAL APPLICABILITY

The present invention provides a recombinant microorganism that synthesizes pyruvic acid, which is a C3 organic compound, at a remarkably improved rate compared to the related art using carbon dioxide, which is abundant in nature, and formic acid, which has low toxicity, is suitable for an assimilation reaction in terms of reaction kinetics, and can be easily and quickly synthesized from carbon dioxide, and in particular, that can grow at a remarkably improved rate even in a medium containing only carbon dioxide and formic acid as carbon sources, without containing glucose. Therefore, the recombinant microorganism according to the present invention has an advantage of synthesizing pyruvic acid and various value-added compounds using the same as an intermediate product in an economically efficient manner.

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying filed claims and equivalents thereto.

What is claimed is:

1. A recombinant microorganism, in which a gene encoding a glycine cleavage system transcriptional repressor, pyruvate formate lyase, or phosphoglycerate dehydrogenase is attenuated or deleted from a host microorganism having a formic acid assimilation pathway,
   a gene encoding an enzyme involved in a glycine cleavage system reaction is enhancely expressed in the host microorganism having the formic acid assimilation pathway, and
   a gene encoding formate-tetrahydrofolate ligase, methenyl tetrahydrofolate cyclohydrolase, or methylene-tetrahydrofolate dehydrogenase is introduced into the host microorganism having the formic acid assimilation pathway.

2. The recombinant microorganism according to claim 1, wherein the host microorganism is selected from the group consisting of *Escherichia, Mannheimia, Rhodobacter* and *Methylobacterium* genera.

3. The recombinant microorganism according to claim 1, wherein the expression of the gene encoding the enzyme involved in the glycine cleavage system reaction is enhanced by substituting a native promoter with a strong promoter.

4. The recombinant microorganism according to claim 3, wherein the strong promoter is selected from the group consisting of a trc promoter, a tac promoter, a T7 promoter, a lac promoter and a trp promoter.

5. The recombinant microorganism according to claim 1, wherein the gene encoding formate-tetrahydrofolate ligase is represented by a nucleotide sequence of SEQ ID NO: 1, the gene encoding methenyl tetrahydrofolate cyclohydrolase is represented by a nucleotide sequence of SEQ ID NO: 2, and the gene encoding methylene-tetrahydrofolate dehydrogenase is represented by a nucleotide sequence of SEQ ID NO: 3.

6. The recombinant microorganism according to claim 1, wherein a gene encoding a phosphoenolpyruvate synthase regulatory protein or phosphoribosylglycinamide formyltransferase is further attenuated or deleted from the recombinant microorganism,
   expression of a gene encoding phosphoenolpyruvate synthase (ppsA) or H$^+$-translocating NAD(P) transhydrogenase (pntAB) is further enhanced in the recombinant microorganism, and
   a gene encoding formate dehydrogenase and/or a mutant thereof is further introduced into the recombinant microorganism.

7. The recombinant microorganism according to claim 6, wherein expression of the gene encoding the phosphoenolpyruvate synthase (ppsA) or H$^+$-translocating NAD(P) transhydrogenase (pntAB) is enhanced by substituting a native promoter with a strong promoter.

8. The recombinant microorganism according to claim 7, wherein the strong promoter is selected from the group consisting of a trc promoter, a tac promoter, a T7 promoter, a lac promoter and a trp promoter.

9. The recombinant microorganism according to claim 6, wherein genes encoding one or more selected from the group consisting of the formate-tetrahydrofolate ligase, the methenyl tetrahydrofolate cyclohydrolase, the methylene-tetrahydrofolate dehydrogenase, the formate dehydrogenase, and the formate dehydrogenase mutant are introduced by being cloned into a vector including an origin of replication having 1 to 12 copies.

10. The recombinant microorganism according to claim 9, wherein the vector includes an origin of replication having 1 to 5 copies.

11. The recombinant microorganism according to claim 9, wherein the gene encoding formate dehydrogenase is represented by a nucleotide sequence of SEQ ID NO: 18, and the gene encoding the formate dehydrogenase mutant is represented by a nucleotide sequence of SEQ ID NO: 21.

12. The recombinant microorganism according to claim 1, wherein the recombinant microorganism is capable of producing a C3 compound using only formic acid and carbon dioxide as carbon sources.

13. The recombinant microorganism according to claim 12, wherein the C3 compound is pyruvic acid.

14. A method for producing a C3 compound comprising:
    (a) a step of culturing the recombinant microorganism according to claim 1 using formic acid and carbon dioxide as carbon sources to produce a C3 compound; and
    (b) a step of collecting the produced C3 compound.

15. The method according to claim 14, wherein 0.02 to 0.08 mM IPTG is added in the step of culturing the recombinant microorganism.

16. The method according to claim 14, wherein the recombinant microorganism is cultured at 31 to 33° C.

17. The method according to claim 14, wherein in the step of culturing, the formic acid is maintained at a concentration of 2 to 3 g/l, and the pH is maintained at 6.6 to 7.0.

18. The method according to claim 14, wherein the recombinant microorganism is initially cultured at a stirring speed of 450 to 550 rpm, and is then cultured while the stirring speed is increased to a final speed of 700 to 800 rpm.

19. A method for producing a useful compound using pyruvic acid as an intermediate product comprising:
    (a) a step of culturing the recombinant microorganism according to claim 1 using formic acid and carbon dioxide as carbon sources to produce a useful substance having a pyruvic acid as an intermediate product; and
    (b) a step of collecting the produced useful substance.

20. The method according to claim 19, wherein the useful substance is selected from the group consisting of butanol, isobutanol, hexanol, heptanol, octanol, nonanol, decanol, tert-butanol, 1-pentanol, 2-pentanol, 3-pentanol, 2-methyl-1-butanol, 3-methyl-1-butanol, 2-methyl-2-butanol, isobutanol, putrescine, L-ornithine, arginine, polycyclic aromatic hydrocarbons (PAHs), polylactate, polylactate-co-glycolate, polyisovalerate, polyhydroxybutyrate (PHB), 4-hydroxybutyrate, biodiesel, gasoline, olefin, 5-aminovaleric acid, gamma-iminobutyric acid, 3-hydroxypyropionic acid, 3-aminopropionic acid, acrylic acid, 1,3-diaminopropane, caprolactam, threonine, valine, isoleucine, fumaric acid, malic acid, succinic acid, ceramide, astaxanthin, silybin, lycopene, lutein, and retinol.

\* \* \* \* \*